United States Patent
Betts

(10) Patent No.: US 7,022,705 B2
(45) Date of Patent: Apr. 4, 2006

(54) ISOXAZOLINE DERIVATIVES USEFUL AS ANTIMICROBIALS

(75) Inventor: Michael John Betts, Macclesfield (GB)

(73) Assignee: AstraZeneca AB, Södertälje (SE)

( * ) Notice: Subject to any disclaimer, the term of this patent is extended or adjusted under 35 U.S.C. 154(b) by 26 days.

(21) Appl. No.: 10/493,707

(22) PCT Filed: Oct. 23, 2002

(86) PCT No.: PCT/GB02/04770

§ 371 (c)(1),
(2), (4) Date: Jan. 28, 2005

(87) PCT Pub. No.: WO03/035073

PCT Pub. Date: May 1, 2003

(65) Prior Publication Data
US 2005/0119317 A1 Jun. 2, 2005

Related U.S. Application Data

(60) Provisional application No. 60/330,587, filed on Oct. 25, 2001.

(51) Int. Cl.
*C07D 413/14* (2006.01)
*A61K 31/497* (2006.01)

(52) U.S. Cl. .......... 514/252.05; 514/226.8; 514/227.8; 514/236.2; 514/254.02; 514/256; 514/269; 544/55; 544/60; 544/96; 544/112; 544/113; 544/238; 544/242; 544/367

(58) Field of Classification Search .......... 544/55, 544/60, 96, 112, 113, 238, 242, 367; 514/226.8, 514/227.8, 236.2, 252.05, 254.02, 256, 269
See application file for complete search history.

(56) References Cited

U.S. PATENT DOCUMENTS

| 3,318,878 | A | | 5/1967 | Dunn |
|---|---|---|---|---|
| 3,769,295 | A | | 10/1973 | Hoyle |
| 5,156,669 | A | * | 10/1992 | Zierke et al. .......... 71/548 |

FOREIGN PATENT DOCUMENTS

| DE | 199 09 785 A1 | 9/2000 |
|---|---|---|
| DE | 199 62 924 A1 | 7/2001 |
| EP | 0 455 052 B1 | 11/1991 |
| EP | 1 227 084 A1 | 7/2002 |
| WO | WO-93/23384 A1 | 11/1993 |
| WO | WO-97/14690 A1 | 4/1997 |
| WO | WO-97/23212 A1 | 7/1997 |
| WO | WO-97/27188 A1 | 7/1997 |
| WO | WO-97/30995 A1 | 8/1997 |
| WO | WO-97/31917 A1 | 9/1997 |
| WO | WO-97/43280 A1 | 11/1997 |

(Continued)

OTHER PUBLICATIONS

Pae, A.N., et al., "Synthesis and In Vitro Activity of New Oxazolidinone Antibacterial Agents Having Substituted Isoxazoles," Bioorganic & Medicinal Chemistry Letters, 9, 2679-2684, (1999).

(Continued)

*Primary Examiner*—Kamal A. Saeed
*Assistant Examiner*—Nyeemah Grazier

(57) ABSTRACT

Compounds of the formula (I), or a pharmaceutically-acceptable salt, or an in-vivo-hydrolysable ester thereof,

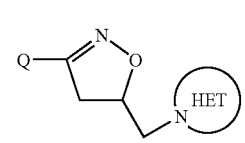

(I)

wherein, for example,
HET is an N-linked 5-membered, fully or partially unsaturated heterocyclic ring, or
HET is an N-linked 6-membered di-hydro-heteroaryl ring;
Q is, for example, Q1 or Q2:

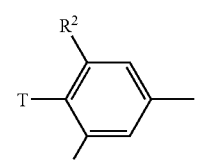

Q1

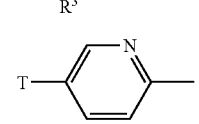

Q2 wherein $R^2$ and $R^3$ are independently hydrogen or fluoro;
T is selected from a range of groups, for example a group of the formula (TC7)

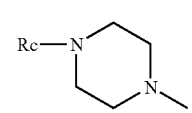

(TC7)

wherein Rc is, for example, hydrogen, $R^{13}CO$—, $R^{13}SO_2$— or $R^{13}CS$—;
wherein $R^{13}$ is, for example, optionally substituted (1–10C)alkyl or $R^{14}C(O)O(1$–$6C)$alkyl
wherein $R^{14}$ is optionally substituted (1–10C)alkyl; are useful as antibacterial agents; and
processes for their manufacture and pharmaceutical compositions containing them are described.

6 Claims, No Drawings

FOREIGN PATENT DOCUMENTS

| | | |
|---|---|---|
| WO | WO-98/01446 A1 | 1/1998 |
| WO | WO-98/01447 A1 | 1/1998 |
| WO | WO-98/07708 A1 | 2/1998 |
| WO | WO-98/15541 A1 | 4/1998 |
| WO | WO-98/57937 A2 | 12/1998 |
| WO | WO-99/10343 A1 | 3/1999 |
| WO | WO-99/11642 A1 | 3/1999 |
| WO | WO-99/10342 A1 | 4/1999 |
| WO | WO-99/28317 A1 | 6/1999 |
| WO | WO-99/41244 A1 | 8/1999 |
| WO | WO-99/43671 A1 | 9/1999 |
| WO | WO-99/64416 A2 | 12/1999 |
| WO | WO-99/64417 A2 | 12/1999 |
| WO | WO-00/10566 A1 | 3/2000 |
| WO | WO-00/21960 A1 | 4/2000 |
| WO | WO-00/41473 A2 | 7/2000 |
| WO | WO-01/07422 A1 | 2/2001 |
| WO | WO-01/26656 A2 | 4/2001 |
| WO | WO-01/40222 A1 | 6/2001 |
| WO | WO-01/40236 A2 | 6/2001 |
| WO | WO-02/081468 A1 | 6/2001 |
| WO | WO-01/81350 A1 | 11/2001 |
| WO | WO-02/48139 A2 | 6/2002 |
| WO | WO-02/056013 A2 | 7/2002 |
| WO | WO-02/080841 A2 | 10/2002 |
| WO | WO-02/081469 A1 | 10/2002 |
| WO | WO-02/096890 A2 | 12/2002 |
| WO | WO-02/096916 A1 | 12/2002 |
| WO | WO-02/096917 A1 | 12/2002 |
| WO | WO-02/096918 A1 | 12/2002 |
| WO | WO-02/102785 A1 | 12/2002 |
| WO | WO-03/008395 A1 | 1/2003 |
| WO | WO-03/022824 A1 | 3/2003 |
| WO | WO-03/035073 A1 | 5/2003 |
| WO | WO-03/035648 A1 | 5/2003 |
| WO | WO-03/072575 A1 | 9/2003 |
| WO | WO-03/072576 A2 | 9/2003 |
| WO | WO 2004029066 A2 * | 4/2004 |

OTHER PUBLICATIONS

Park, C.H., et al., "Antibacterials. Synthesis and Structure-Activity Studies of 3-Aryl-2-oxooxazolidines. 4. Multiply-Substituted Aryl Derivatives," J. Med. Chem., 35, 1156-1165 (1992).

Gregory, W.A., et al., "Antibacterials. Synthesis and Structure-Activity Studies of 3-Aryl-2-oxooxazolidines. 2. The 'A' Group," J. Med. Chem., 33, 2569-2578 (1990).

Skacani, I., et al., "The preparation and fungicidal activity of a series of 1-[(3-arylisoxazolin- or isoxazol-5-yl)methyl]-1H-1,2,4-triazoles," Chem. Papers, 45(6), 807-815 (1991).

* cited by examiner

ISOXAZOLINE DERIVATIVES USEFUL AS ANTIMICROBIALS

RELATED APPLICATIONS

This application is a national stage filing under 35 U.S.C. 371 of International Application No. PCT/GB02/04770, filed Oct. 23, 2002, which claims priority from Provisional Application No. 60/330,587, filed Oct. 25, 2001, the specification of which is incorporated by reference herein. International Application No. PCT/GB02/04770 was published under PCT Article 21(2) in English.

The present invention relates to antibiotic compounds and in particular to antibiotic compounds containing a substituted isoxazoline ring. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded as effective against both Gram-positive and certain Gram-negative pathogens.

Gram-positive pathogens, for example Staphylococci, Enterococci, and Streptococci are particularly important because of the development of resistant strains which are both difficult to treat and difficult to eradicate from the hospital environment once established. Examples of such strains are methicillin resistant *staphylococcus* (MRSA), methicillin resistant coagulase negative staphylococci (MRCNS), penicillin resistant *Streptococcus pneumoniae* and multiply resistant *Enterococcus faecium*.

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens. There is also now increasing resistance appearing towards agents such as β-lactams, quinolones and macrolides used for the treatment of upper respiratory tract infections, also caused by certain Gram negative strains including *H. influenzae* and *M. catarrhalis*.

Certain antibacterial compounds containing an oxazolidinone ring have been described in the art (for example, Walter A. Gregory et al in J. Med. Chem. 1990, 33, 2569–2578 and Chung-Ho Park et al in J. Med. Chem. 1992, 35, 1156–1165). Such antibacterial oxazolidinone compounds with a 5-acetamidomethyl sidechain may be subject to mammalian peptidase metabolism. Furthermore, bacterial resistance to known antibacterial agents may develop, for example, by (i) the evolution of active binding sites in the bacteria rendering a previously active pharmacophore less effective or redundant, (ii) the evolution of means to chemically deactivate a given pharmacophore and/or (iii) the development and/or up-regulation of efflux mechanisms. Therefore, there remains an ongoing need to find new antibacterial agents with a favourable pharmacological profile, in particular for compounds containing new pharmacophores.

We have discovered a new class of antibiotic compounds containing an aryl substituted isoxazoline ring in which the aryl ring is itself further substituted. These compounds have useful activity against Gram-positive pathogens including MRSA and MRCNS and, in particular, against various strains exhibiting resistance to vancomycin and against *E. faecium* strains resistant to both aminoglycosides and clinically used β-lactams, but also to fastidious Gram negative strains such as *H. influenzae* and *M. catarrhalis* strains.

Accordingly the present invention provides a compound of the formula (I), or a pharmaceutically-acceptable salt, or an in-vivo-hydrolysable ester thereof,

(I)

wherein

HET is an N-linked 5-membered, fully or partially unsaturated heterocyclic ring, containing either (i) 1 to 3 further nitrogen heteroatoms or (ii) a further heteroatom selected from O and S together with an optional further nitrogen heteroatom; which ring is optionally substituted on a C atom, other than a C atom adjacent to the linking N atom, by an oxo or thioxo group; and/or which ring is optionally substituted on any available C atom, other than a C atom adjacent to the linking N atom, by a substituent Rs wherein;

Rs is selected from the group (Rsa) halogen, (1–4C)alkoxy, (2–4C)alkenyloxy, (2–4C)alkenyl, (2–4C)alkynyl, (3–6C)cycloalkyl, (3–6C)cycloalkenyl, amino, (1–4C)alkylamino, di-(1–4C)alkylamino, (2–4C)alkenylamino, (1–4C)alkylcarbonylamino, (1–4C)alkylthiocarbonylamino, (1–4C)alkyl-OCO—NH—, (1–4C)alkyl-NH—CO—NH—, (1–4C)alkyl-NH—CS—NH—, (1–4C)alkyl-SO₂—NH— or (1–4C)alkyl-S(O)q— (wherein q is 0, 1 or 2);

or Rs is selected from the group (Rsb) (1–4C)alkyl group which is optionally substituted by one substituent selected from hydroxy, (1–4C)alkoxy, amino, cyano, azido, (2–4C)alkenyloxy, (1–4C)alkylcarbonyl, (1–4C)alkoxycarbonyl, (1–4C)alkylamino, (2–4C)alkenylamino, (1–4C)alkyl-SO₂—NH—, (1–4C)alkylcarbonylamino, (1–4C)alkylthiocarbonylamino, (1–4C)alkyl-OCO—NH—, (1–4C)alkyl-NH—CO—NH—, (1–4C)alkyl-NH—CS—NH—, (1–4C)alkyl-SO₂—NH—, (1–4C)alkyl-S(O)q— (wherein q is 0, 1 or 2), (3–6C)cycloalkyl, (3–6C)cycloalkenyl, or an N-linked 5-membered heteroaryl ring, which ring contains either (i) 1 to 3 further nitrogen heteroatoms or (ii) a further heteroatom selected from O and S together with an optional further nitrogen heteroatom; which ring is optionally substituted on a carbon atom by an oxo or thioxo group; and/or the ring is optionally substituted on a carbon atom by 1 or 2(1–4C)alkyl groups; and/or on an available nitrogen atom (provided that the ring is not thereby quaternised) by (1–4C)alkyl;

or Rs is selected from a group of formula (Rsc1) to (Rsc3):—

(Rsc1) a fully saturated 4-membered monocyclic ring containing 1 or 2 heteroatoms independently selected from O, N and S (optionally oxidised), and linked via a ring nitrogen or carbon atom; or (Rsc2) a saturated or unsaturated 5-membered monocyclic ring containing 1 heteroatom selected from O, N and S (optionally oxidised), and linked via a ring nitrogen atom if the ring is not thereby quaternised, or a ring carbon atom; or (Rsc3) a saturated or unsaturated 6- to 8-membered monocyclic ring containing 1 or 2 heteroatoms independently selected from O, N and S (optionally oxidised), and linked via a ring nitrogen atom if the ring is not thereby quaternised, or a ring carbon atom;

wherein said rings in (Rsc1) to (Rsc3) are optionally substituted on an available carbon atom by 1 or 2 substituents independently selected from hydroxy, (1–4C)alkoxy, amino, cyano, azido, (2–4C)alkenyloxy, (1–4C)alkylcarbonyl, (1–4C)alkoxycarbonyl, (1–4C)alkylamino, (2–4C)alkenylamino, (1–4C)alkyl-SO$_2$—NH—, (1–4C)alkylcarbonylamino, (1–4C)alkylthiocarbonylamino, (1–4C)alkyl-OCO—NH—, (1–4C)alkyl-NH—CO—NH—, (1–4C)alkyl-NH—CS—NH—, (1–4C)alkyl-SO$_2$—NH—, (1–4C)alkyl-S(O)q— (wherein q is 0, 1 or 2), (3–6C)cycloalkyl or (3–6C)cycloalkenyl;

or Rs is selected from the group (Rsd) cyano, nitro, azido, formyl, (1–4C)alkylcarbonyl or (1–4C)alkoxycarbonyl; and wherein at each occurrence of an Rs substituent containing an alkyl, alkenyl, alkynyl, cycloalkyl or cycloalkenyl moiety in (Rsa), (Rsb) or (Rsc1) to (Rsc3) each such moiety is optionally further substituted on an available carbon atom with one or more substituents independently selected from F, Cl and Br and/or by one cyano group;

and/or which ring is optionally substituted on an available nitrogen atom (provided that the ring is not thereby quaternised) by (1–4C)alkyl;

or

HET is an N-linked 6-membered di-hydro-heteroaryl ring containing up to three nitrogen heteroatoms in total (including the linking heteroatom), which ring is substituted on a suitable C atom, other than a C atom adjacent to the linking N atom, by oxo or thioxo and/or which ring is optionally substituted on any available C atom, other than a C atom adjacent to the linking N atom, by one or two substituents Rs, wherein Rs is as hereinbefore defined, and/or on an available nitrogen atom (provided that the ring is not thereby quaternised) by (1–4C)alkyl; and wherein at each occurrence of alkyl, alkenyl and cycloalkyl HET substituents, each is optionally substituted with one or more substituents independently selected from F, Cl and Br and/or by one cyano group;

Q is selected from Q1 to Q10:—

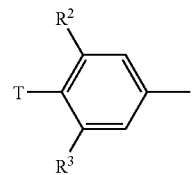
Q1

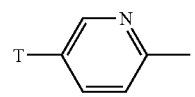
Q2

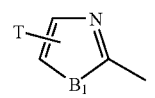
Q3

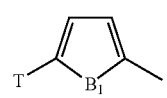
Q4

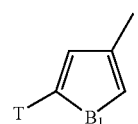
Q5

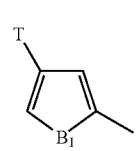
Q6

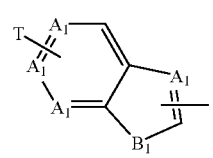
Q7

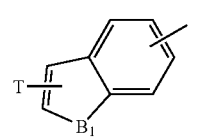
Q8

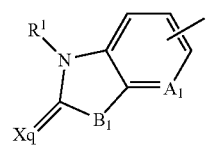
Q9

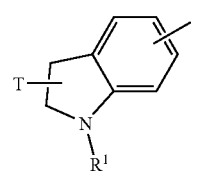
Q10 wherein $R^2$ and $R^3$ are independently hydrogen or fluoro;

wherein $A_1$ is carbon or nitrogen; $B_1$ is O or S (or, in Q9 only, NH); $X_q$ is O, S or N—$R^1$ (wherein $R^1$ is hydrogen, (1–4C)alkyl or hydroxy-(1–4C)alkyl); and wherein in Q7 each $A_1$ is independently selected from carbon or nitrogen, with a maximum of 2 nitrogen heteroatoms in the 6-membered ring, and Q7 is linked to T via any of the $A_1$ atoms (when $A_1$ is carbon), and linked in the 5-membered ring via the specified carbon atom, or via $A_1$ when $A_1$ is carbon; Q8 and Q10 are linked to T via either of the specified carbon atoms in the 5-membered ring, and linked in the benzo-ring via either of the two specified carbon atoms on either side of the linking bond shown; and Q9 is linked via either of the two specified carbon atoms on either side of the linking bond shown;

wherein T is selected from the groups in (TA) to (TE) below (wherein AR1, AR2, AR2a, AR2b, AR3, AR3a, AR3b, AR4, AR4a, CY1 and CY2 are defined hereinbelow);

(TA) T is selected from the following groups:—

(TAa) AR1, AR1-(1–4C)alkyl-, AR2 (carbon linked), AR3;

(TAb) AR1-CH(OH), AR2-CH(OH)—, AR3-CH(OH)—;

(TAc) AR1-CO—, AR2-CO—, AR3-CO—, AR4-CO—;

(TAd) AR1-O—, AR2-O—, AR3-O—;

(TAe) AR1-S(O)$_q$—, AR2-S(O)$_q$—, AR3-S(O)$_q$— (q is 0, 1 or 2);

(TAf) an optionally substituted N-linked (fully unsaturated) 5-membered heteroaryl ring system containing 1, 2 or 3 nitrogen atoms;

(TAg) a carbon linked tropol-3-one or tropol-4-one, optionally substituted in a position not adjacent to the linking position; or (TB) T is selected from the following groups:—

(TBa) halo or (1–4C)alkyl {optionally substituted by one or more groups each independently selected from hydroxy, (1–4C)alkoxy, (1–4C)alkanoyl, cyano, halo, trifluoromethyl, (1–4C)alkoxycarbonyl, —NRvRw, (1–6C)alkanoylamino, (1–4C)alkoxycarbonylamino, N—(1–4C)alkyl-N—(1–6C)alkanoylamino, (1–4C)alkylS(O)$_q$— (q is 0, 1 or 2), CY1, CY2 or AR1};

(TBb) —NRv$^1$Rw$^1$;

(TBc) ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl, 2-(AR2)ethenyl;

(TBd) R$^{10}$CO—, R$^{10}$S(O)$_q$— (q is 0, 1 or 2) or R$^{10}$CS— wherein R$^{10}$ is selected from the following groups:—

(TBda) CY1 or CY2;

(TBdb) hydrogen, (1–4C)alkoxycarbonyl, trifluoromethyl, —NRvRw, ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl or 2-(AR2)ethenyl; or (TBdc) (1–4C)alkyl {optionally substituted as defined in (TBa) above, or by (1–4C)alkylS(O)$_p$NH— or (1–4C)alkylS(O)$_p$—((1–4C)alkyl)N— (p is 1 or 2)};

wherein Rv is hydrogen or (1–4C)alkyl; Rw is hydrogen or (1–4C)alkyl; Rv$^1$ is hydrogen, (1–4C)alkyl or (3–8C)cycloalkyl; Rw$^1$ is hydrogen, (1–4C)alkyl, (3–8C)cycloalkyl, (1–4C)alkyl-CO— or (1–4C)alkylS(O)$_q$— (q is 1 or 2); or (TC) T is selected from the following groups:—

(TCa) an optionally substituted, fully saturated 4-membered monocyclic ring containing 1 or 2 heteroatoms independently selected from O, N and S (optionally oxidised), and linked via a ring nitrogen or sp$^3$ carbon atom;

(TCb) an optionally substituted 5-membered monocyclic ring containing 1 heteroatom selected from O, N and S (optionally oxidised), and linked via a ring nitrogen atom or a ring sp$^3$ or sp$^2$ carbon atom, which monocyclic ring is fully saturated other than (where appropriate) at a linking sp$^2$ carbon atom;

(TCc) an optionally substituted 6- to 8-membered monocyclic ring containing 1 or 2 heteroatoms independently selected from O, N and S (optionally oxidised), and linked via a ring nitrogen atom or a ring sp$^3$ or sp$^2$ carbon atom, which monocyclic ring is fully saturated other than (where appropriate) at a linking sp$^2$ carbon atom; or (TD) T is selected from the following groups:—

(TDa) a bicyclic spiro-ring system containing 0, 1 or 2 ring nitrogen atoms as the only ring heteroatoms, the structure consisting of a 5- or 6-membered ring system (linked via a ring nitrogen atom or a ring sp$^3$ or sp$^2$ carbon atom) substituted (but not adjacent to the linking position) by a 3-, 4- or 5-membered spiro-carbon-linked ring; which bicyclic ring system is (i) fully saturated other than (where appropriate) at a linking sp$^2$ carbon atom;

(ii) contains one —N(Rc)— group in the ring system (at least two carbon atoms away from the linking position when the link is via a nitrogen atom or an sp$^2$ carbon atom) or one —N(Rc)— group in an optional substituent (not adjacent to the linking position) and is (iii) optionally further substituted on an available ring carbon atom; or (TDb) a 7-, 8- or 9-membered bicyclic ring system (linked via a ring nitrogen atom or a ring sp$^3$ or sp$^2$ carbon atom) containing 0, 1 or 2 ring nitrogen atoms (and optionally a further O or S ring heteroatom), the structure containing a bridge of 0, 1 or 2 carbon atoms; which bicyclic ring system is (i) fully saturated other than (where appropriate) at a linking sp$^2$ carbon atom;

(ii) contains one O or S heteroatom, or one —N(Rc)— group in the ring (at least two carbon atoms away from the linking position when the link is via a nitrogen atom or an sp$^2$ carbon atom) or one —N(Rc)— group in an optional substituent (not adjacent to the linking position) and is (iii) optionally further substituted on an available ring carbon atom; or (TE) T is selected from the following groups (TE1) to (TE3):—

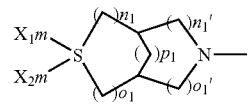
(TE1)

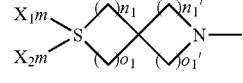
(TE2)

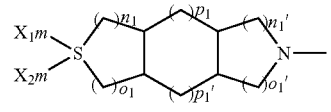
(TE3)

wherein:

$X_{1m}$ and $X_{2m}$ taken together represent $R_{2s}$—(E)$_{ms}$—N=; or $X_{1m}$ is O= and $X_{2m}$ is $R_{2s}$—(E)$_{ms}$—N—, and vice versa;

wherein E is an electron withdrawing group selected from —SO$_2$—, —CO—, —O—CO—, —CO—O—, —CS—, —CON(R$_s$)—, —SO$_2$N(R$_s$)—, or E may represent a group of the formula $R_{3s}$—C(=N—O—$R_{3s}$)—C(=O)—, wherein $R_{3s}$ is H or as defined in $R_{2s}$ at (i) below;

or, when E is —CON($R_s$)— or —$SO_2$N($R_s$)—, $R_{2s}$ and $R_s$ may link together to form a carbon chain which defines a 5- or 6-membered saturated, unsaturated or partially unsaturated ring linked via the N atom in E, which ring is optionally further substituted by an oxo substituent, and which ring may be optionally fused with a phenyl group to form a benzo-fused system, wherein the phenyl group is optionally substituted by up to three substituents independently selected from halo, cyano, (1–4C)alkyl and (1–4C)alkoxy; ms is 0 or 1;

$R_{2s}$ and $R_s$ are independently selected from:
(i) hydrogen (except where E is —$SO_2$— or —O—CO—), or (1–6C)alkyl {optionally substituted by one or more (1–4C)alkanoyl groups (including geminal disubstitution) and/or optionally monosubstituted by cyano, cyanoimino, (1–4C)alkoxy, trifluoromethyl, (1–4C)alkoxycarbonyl, phenyl (optionally substituted as defined for AR1 hereinafter), optionally substituted heteroaryl group of the formula AR2, AR2a, AR2b, AR3, AR3a, AR3b, AR4, AR4a or CY1 all as defined (and optionally substituted as defined) hereinafter, (1–4C)alkylS(O)$_q$— (q is 0, 1 or 2); and/or (with the proviso that where $R_{2s}$ is —$SO_2$ or —O—CO— not on the first carbon atom of the (1–6C) alkyl chain) optionally substituted by one or more groups (including geminal disubstitution) each independently selected from hydroxy and fluoro, and/or optionally further substituted, by no more than one of each of, oxo, —NRvRw [wherein Rv is hydrogen or (1–4C)alkyl; Rw is hydrogen or (1–4C)alkyl], (1–6C)alkanoylamino, (1–4C)alkoxycarbonylamino, N—(1–4C)alkyl-N—(1–6C)alkanoylamino, (1–4C)alkylS(O)$_p$NH— or (1–4C)alkylS(O)$_p$—((1–4C)alkyl)N— (p is 1 or 2)}; or
(ii) an optionally substituted aryl or optionally substituted heteroaryl group of the formula AR1, AR2, AR2a, AR2b, AR3, AR3a, AR3b, AR4, AR4a or CY1 all as defined (and optionally substituted as defined) hereinafter; or (where ms is 0 only);
(iii) cyano, —CO—NRvRw, —CO—NRvRw', —$SO_2$—NRvRw, —$SO_2$—NRv Rw' [wherein Rv is hydrogen or (1–4C)alkyl; Rw is hydrogen or (1–4C)alkyl; Rw' is phenyl (optionally substituted as defined for AR1 hereinafter), or a heteroaryl group selected from AR2, AR2a, AR2b, AR3, AR3a, AR3b, AR4, AR4a (optionally substituted as defined hereinafter)], (1–4C)alkoxycarbonyl, trifluoromethyl, ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl, 2-(AR2)ethenyl, or 2-(AR2a)ethenyl; and wherein ( )$n_1$, ( )$o_1$, ( )$n_{1'}$, ( )$o_{1'}$, ( )$p_1$ and ( )$p_{1'}$ represent chains of carbon atoms (optionally substituted as defined for AR1 hereinafter) of length $n_1$, $o_1$, $n_{1'}$, $o_{1'}$, $p_1$ and $p_{1'}$ respectively, and are independently 0–2, with the proviso that in (TE1) and (TE2) the sum of $n_1$, $o_1$, $n_{1'}$ and $o_{1'}$ does not exceed 8 (giving a maximum ring size of 14 in (TE1) and 11 in (TE2)), and in (TE3) the sum of $n_1$, $o_1$, $n_{1'}$, $o_{1'}$, $p_1$ and $p_{1'}$ does not exceed 6 (giving a maximum ring size of 12).

wherein Rc is selected from groups (Rc1) to (Rc5):—
(Rc1) (1–6C)alkyl {optionally substituted by one or more (1–4C)alkanoyl groups (including geminal disubstitution) and/or optionally monosubstituted by cyano, (1–4C)alkoxy, trifluoromethyl, (1–4C)alkoxycarbonyl, phenyl (optionally substituted as for AR1 defined hereinafter), (1–4C)alkylS(O)$_q$— (q is 0, 1 or 2); or, on any but the first carbon atom of the (1–6C)alkyl chain, optionally substituted by one or more groups (including geminal disubstitution) each independently selected from hydroxy and fluoro, and/or optionally monosubstituted by oxo, —NRvRw [wherein Rv is hydrogen or (1–4C)alkyl; Rw is hydrogen or (1–4C)alkyl], (1–6C)alkanoylamino, (1–4C)alkoxycarbonylamino, N—(1–4C)alkyl-N—(1–6C)alkanoylamino, (1–4C)alkylS(O)$_p$NH— or (1–4C)alkylS(O)$_p$—((1–4C)alkyl)N— (p is 1 or 2)};
(Rc2) $R^{13}$CO—, $R^{13}SO_2$— or $R^{13}$CS—
wherein $R^{13}$ is selected from (Rc2a) to (Rc2e):—
(Rc2a) AR1, AR2, AR2a, AR2b, AR3, AR3a, AR3b, AR4, AR4a, CY1, CY2;
(Rc2b) hydrogen, (1–4C)alkoxycarbonyl, trifluoromethyl, —NRvRw [wherein Rv is hydrogen or (1–4C)alkyl; Rw is hydrogen or (1–4C)alkyl], ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl, 2-(AR2)ethenyl, 2-(AR2a)ethenyl;
(Rc2c) (1–10C)alkyl {optionally substituted by one or more groups (including geminal disubstitution) each independently selected from hydroxy, (1–10C)alkoxy, (1–4C)alkoxy-(1–4C)alkoxy, (1–4C)alkoxy-(1–4C)alkoxy-(1–4C)alkoxy, (1–4C)alkanoyl, carboxy, phosphoryl [—O—P(O)(OH)$_2$, and mono- and di-(1–4C)alkoxy derivatives thereof], phosphiryl [—O—P(OH)$_2$ and mono- and di-(1–4C)alkoxy derivatives thereof], and amino; and/or optionally substituted by one group selected from phosphonate [phosphono, —P(O)(OH)$_2$, and mono- and di-(1–4C)alkoxy derivatives thereof], phosphinate [—P(OH)$_2$ and mono- and di-(1–4C)alkoxy derivatives thereof], cyano, halo, trifluoromethyl, (1–4C)alkoxycarbonyl, (1–4C)alkoxy-(1–4C)alkoxycarbonyl, (1–4C)alkoxy-(1–4C)alkoxy-(1–4C)alkoxycarbonyl, (1–4C)alkylamino, di((1–4C)alkyl)amino, (1–6C)alkanoylamino, (1–4C)alkoxycarbonylamino, N-(1–4C)alkyl-N-(1–6C)alkanoylamino, (1–4C)alkylaminocarbonyl, di((1–4C)alkyl)aminocarbonyl, (1–4C)alkylS(O)$_p$NH—, (1–4C)alkylS(O)$_p$—((1–4C)alkyl)N—, fluoro(1–4C)alkylS(O)$_p$NH—, fluoro(1–4C)alkylS(O)$_p$((1–4C)alkyl)N—, (1–4C)alkylS(O)$_q$— [the (1–4C)alkyl group of (1–4C)alkylS(O)$_q$— being optionally substituted by one substituent selected from hydroxy, (1–4C)alkoxy, (1–4C)alkanoyl, phosphoryl [—O—P(O)(OH)$_2$, and mono- and di-(1–4C)alkoxy derivatives thereof], phosphiryl [—O—P(OH)$_2$ and mono- and di-(1–4C)alkoxy derivatives thereof], amino, cyano, halo, trifluoromethyl, (1–4C)alkoxycarbonyl, (1–4C)alkoxy-(1–4C)alkoxycarbonyl, (1–4C)alkoxy-(1–4C)alkoxy-(1–4C)alkoxycarbonyl, carboxy, (1–4C)alkylamino, di((1–4C)alkyl)amino, (1–6C)alkanoylamino, (1–4C)alkoxycarbonylamino, N-(1–4C)alkyl-N-(1–6C)alkanoylamino, (1–4C)alkylaminocarbonyl, di((1–4C)alkyl)aminocarbonyl, (1–4C)alkylS(O)$_p$NH—, (1–4C)alkylS(O)$_p$—((1–4C)alkyl)N—, (1–4C)alkylS(O)$_q$—, AR1-S(O)$_q$—, AR2-S(O)$_q$—, AR3-S(O)$_q$— and also AR2a, AR2b, AR3a and AR3b versions of AR2 and AR3 containing groups], CY1, CY2, AR1, AR2, AR3, AR1-O—, AR2-O—, AR3-O—, AR1-S(O)$_q$—, AR2-S(O)$_q$—, AR3-S(O)$_q$—, AR1-NH—, AR2-

NH—, AR3-NH— (p is 1 or 2 and q is 0, 1 or 2), and also AR2a, AR2b, AR3a and AR3b versions of AR2 and AR3 containing groups};

(Rc2d) $R^{14}C(O)O(1-6C)$alkyl wherein $R^{14}$ is AR1, AR2, (1–4C)alkylamino (the (1–4C)alkyl group being optionally substituted by (1–4C)alkoxycarbonyl or by carboxy), benzyloxy-(1–4C)alkyl or (1–10C)alkyl {optionally substituted as defined for (Rc2c)};

(Rc2e) $R^{15}O$— wherein $R^{15}$ is benzyl, (1–6C)alkyl {optionally substituted as defined for (Rc2c)}, CY1, CY2 or AR2b;

(Rc3) hydrogen, cyano, 2-cyanoethenyl, 2-cyano-2-((1–4C)alkyl)ethenyl, 2-((1–4C)alkylaminocarbonyl)ethenyl, 2-((1–4C)alkoxycarbonyl)ethenyl, 2-nitroethenyl, 2-nitro-2-((1–4C)alkyl)ethenyl, 2-(AR1)ethenyl, 2-(AR2)ethenyl, or of the formula

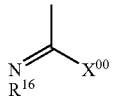

(Rc3a)

wherein $X^{00}$ is —$OR^{17}$, —$SR^{17}$, —$NHR^{17}$ and —$N(R^{17})_2$; wherein $R^{17}$ is hydrogen (when $X^{00}$ is —$NHR^{17}$ and —$N(R^{17})_2$), and $R^{17}$ is (1–4C)alkyl, phenyl or AR2 (when $X^{00}$ is —$OR^{17}$, —$SR^{17}$ and —$NHR^{17}$); and $R^{16}$ is cyano, nitro, (1–4C)alkylsulfonyl, (4–7C)cycloalkylsulfonyl, phenylsulfonyl, (1–4C)alkanoyl and (1–4C)alkoxycarbonyl;

(Rc4) trityl, AR1, AR2, AR2a, AR2b, AR3, AR3a, AR3b;

(Rc5) RdOC(Re)=CH(C=O)—, RfC(=O)C(=O)—, RgN=C(Rh)C(=O)— or RiNHC(Rj)=CHC(=O)— wherein Rd is (1–6C)alkyl; Re is hydrogen or (1–6C)alkyl, or Rd and Re together form a (3–4C)alkylene chain; Rf is hydrogen, (1–6C)alkyl, hydroxy(1–6C)alkyl, (1–6C)alkoxy(1–6C)alkyl, —NRvRw [wherein Rv is hydrogen or (1–4C)alkyl; Rw is hydrogen or (1–4C)alkyl], (1–6C)alkoxy, (1–6C)alkoxy(1–6C)alkoxy, hydroxy(2–6C)alkoxy, (1–4C)alkylamino(2–6C)alkoxy, di-(1–4C)alkylamino(2–6C)alkoxy; Rg is (1–6C)alkyl, hydroxy or (1–6C)alkoxy; Rh is hydrogen or (1–6C)alkyl; Ri is hydrogen, (1–6C)alkyl, AR1, AR2, AR2a, AR2b and Rj is hydrogen or (1–6C)alkyl;

wherein

AR1 is an optionally substituted phenyl or optionally substituted naphthyl;

AR2 is an optionally substituted 5- or 6-membered, fully unsaturated (i.e with the maximum degree of unsaturation) monocyclic heteroaryl ring containing up to four heteroatoms independently selected from O, N and S (but not containing any O—O, O—S or S—S bonds), and linked via a ring carbon atom, or a ring nitrogen atom if the ring is not thereby quaternised;

AR2a is a partially hydrogenated version of AR2 (i.e. AR2 systems retaining some, but not the full, degree of unsaturation), linked via a ring carbon atom or linked via a ring nitrogen atom if the ring is not thereby quaternised;

AR2b is a fully hydrogenated version of AR2 (i.e. AR2 systems having no unsaturation), linked via a ring carbon atom or linked via a ring nitrogen atom;

AR3 is an optionally substituted 8-, 9- or 10-membered, fully unsaturated (i.e with the maximum degree of unsaturation) bicyclic heteroaryl ring containing up to four heteroatoms independently selected from O, N and S (but not containing any O—O, O—S or S—S bonds), and linked via a ring carbon atom in either of the rings comprising the bicyclic system;

AR3a is a partially hydrogenated version of AR3 (i.e. AR3 systems retaining some, but not the full, degree of unsaturation), linked via a ring carbon atom, or linked via a ring nitrogen atom if the ring is not thereby quaternised, in either of the rings comprising the bicyclic system;

AR3b is a fully hydrogenated version of AR3 (i.e. AR3 systems having no unsaturation), linked via a ring carbon atom, or linked via a ring nitrogen atom, in either of the rings comprising the bicyclic system;

AR4 is an optionally substituted 13- or 14-membered, fully unsaturated (i.e with the maximum degree of unsaturation) tricyclic heteroaryl ring containing up to four heteroatoms independently selected from O, N and S (but not containing any O—O, O—S or S—S bonds), and linked via a ring carbon atom in any of the rings comprising the tricyclic system;

AR4a is a partially hydrogenated version of AR4 (i.e. AR4 systems retaining some, but not the full, degree of unsaturation), linked via a ring carbon atom, or linked via a ring nitrogen atom if the ring is not thereby quaternised, in any of the rings comprising the tricyclic system;

CY1 is an optionally substituted cyclobutyl, cyclopentyl or cyclohexyl ring;

CY2 is an optionally substituted cyclopentenyl or cyclohexenyl ring.

In another embodiment, the present invention provides a compound of the formula (I) as hereinbefore described, or a pharmaceutically-acceptable salt, or an in-vivo hydrolysable ester thereof, wherein:

HET is an N-linked 5-membered, fully or partially unsaturated heterocyclic ring, containing either (i) 1 to 3 further nitrogen heteroatoms or (ii) a further heteroatom selected from O and S together with an optional further nitrogen heteroatom; which ring is optionally substituted on a C atom, other than a C atom adjacent to the linking N atom, by an oxo or thioxo group; and/or which ring is optionally substituted on any available C atom, other than a C atom adjacent to the linking N atom, by a substituent selected from (1–4C)alkyl, (2–4C)alkenyl, (3–6C)cycloalkyl, amino, (1–4C)alkylamino, di-(1–4C)alkylamino, (1–4C)alkylthio, (1–4C)alkoxy, (1–4C)alkoxycarbonyl, halogen, cyano and trifluoromethyl and/or on an available nitrogen atom (provided that the ring is not thereby quaternised) by (1–4C)alkyl; or HET is an N-linked 6-membered di-hydro-heteroaryl ring containing up to three nitrogen heteroatoms in total (including the linking heteroatom), which ring is substituted on a suitable C atom, other than a C atom adjacent to the linking N atom, by oxo or thioxo and/or which ring is optionally substituted on any available C atom, other than a C atom adjacent to the linking N atom, by one or two substituents independently selected from (1–4C)alkyl, (2–4C)alkenyl, (3–6C)cycloalkyl, amino, (1–4C)alkylamino, di-(1–4C)alkylamino, (1–4C)alkylthio, (1–4C)alkoxy, (1–4C)alkoxycarbonyl, halogen, cyano and trifluoromethyl and/or on an available nitrogen atom (provided that the ring is not thereby quaternised) by (1–4C)alkyl; and wherein at each occurrence of alkyl, alkenyl and cycloalkyl HET substituents, each is optionally substituted with one or more F, Cl or CN;

For the avoidance of doubt in the definition of (TE), and (TC12) & (TC13) herein, it is to be understood that when $R_{2s}$ and $R_s$ are independently selected from (ii) (1–6C)alkyl {optionally substituted, for example, by no more than one of each of oxo and —NRvRw [wherein Rv is hydrogen or (1–4C)alkyl; Rw is hydrogen or (1–4C)alkyl], to avoid duplication with the substituent —CO—NRvRw provided in section (iii) of the definition for $R_{2s}$ and $R_s$, then oxo and —NRvRw are not to be both selected together when (1–6C)alkyl is methyl.

In this specification, HET as an N-linked 5-membered ring may be a fully or partially unsaturated heterocyclic ring, provided there is some degree of unsaturation in the ring.

Particular examples of N-linked 5-membered heteroaryl rings containing 2 to 4 heteroatoms independently selected from N, O and S (with no O—O, O—S or S—S bonds) are preferably rings containing 2 to 4 N atoms, in particular pyrazole, imidazole, 1,2,3-triazole (preferably 1,2,3-triazol-1-yl), 1,2,4-triazole (preferably 1,2,4-triazol-1-yl) and tetrazole (preferably tetrazol-2-yl).

Particular examples of N-linked 6-membered di-hydro-heteroaryl rings containing up to three nitrogen heteroatoms in total (including the linking heteroatom) include di-hydro versions of pyrimidine, pyridazine, pyrazine, 1,2,3-triazine, 1,2,4-triazine, 1,3,5-triazine and pyridine.

In this specification, where it is stated that a ring may be linked via an sp² carbon atom, which ring is fully saturated other than (where appropriate) at a linking sp² carbon atom, it is to be understood that the ring is linked via one of the carbon atoms in a C═C double bond.

In this specification, for (TAa) When T is AR2 (carbon linked), i.e. an optionally substituted 5- or 6-membered, fully unsaturated (i.e with the maximum degree of unsaturation) monocyclic heteroaryl ring containing up to four heteroatoms independently selected from O, N and S (but not containing any O—O, O—S or S—S bonds), it is preferably an optionally substituted C-linked (fully unsaturated) 5-membered heteroaryl ring system containing 1, 2 or 3 heteroatoms drawn in combination from O, N, or S, optionally substituted in a position not adjacent to the linking position. Yet more preferably, (TAa) when AR2, is selected from a group of formula (TAa1) to (TAa6) below (particularly (TAa1), and (TAa2), and especially (TAa1)).

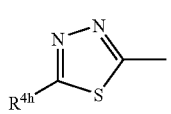
(TAa1)

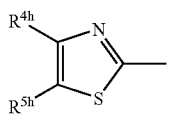
(TAa2)

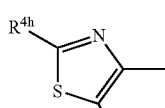
(TAa3)

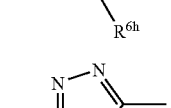
(TAa4)

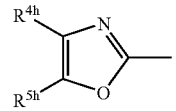
(TAa5)

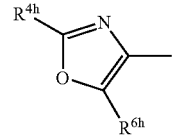
(TAa6)

wherein:

$R^{6h}$ is selected from hydrogen, (1–4C)alkyl, (1–4C)alkoxycarbonyl, (1–4C)alkanoyl, carbamoyl and cyano;

$R^{4h}$ and $R^{5h}$ are independently selected from hydrogen, halo, trifluoromethyl, cyano, nitro, (1–4C)alkoxy, (1–4C)alkylS(O)$_q$— (q is 0, 1 or 2), (1–4C)alkanoyl, (1–4C)alkoxycarbonyl, benzyloxy-(1–4C)alkyl, (2–4C)alkanoylamino, —CONRcRv and —NRcRv wherein any (1–4C)alkyl group contained in the preceding values for $R^{4h}$ and $R^{5h}$ is optionally substituted by up to three substituents independently selected from hydroxy (not on C1 of an alkoxy group, and excluding geminal disubstitution), oxo, trifluoromethyl, cyano, nitro, (1–4C)alkoxy, (2–4C)alkanoyloxy, hydroxyimino, (1–4C)alkoxyimino, (1–4C)alkylS(O)$_q$— (q is 0, 1 or 2), (1–4C)alkylSO$_2$—NRv—, (1–4C)alkoxycarbonyl, —CONRcRv, and —NRcRv (not on C1 of an alkoxy group, and excluding geminal disubstitution); wherein Rv is hydrogen or (1–4C)alkyl and Rc is as hereinbefore defined;

$R^{4h}$ and $R^{5h}$ may further be independently selected from (1–4C)alkyl {optionally substituted by up to three substituents independently selected from hydroxy (excluding geminal disubstitution), oxo, trifluoromethyl, cyano, nitro, (1–4C)alkoxy, (2–4C)alkanoyloxy, hydroxyimino, (1–4C)alkoxyimino, (1–4C)alkylS(O)$_q$— (q is 0, 1 or 2), (1–4C)alkylSO$_2$—NRv—, (1–4C)alkoxycarbonyl, —CONRcRv, and —NRcRv (excluding geminal disubstitution); wherein Rv is hydrogen or (1–4C)alkyl}; Rc is as hereinbefore defined; and wherein any (1–4C)alkyl group contained in the immediately preceding optional substituents (when $R^{4h}$ and $R^{5h}$ are independently (1–4C)alkyl) is itself optionally substituted by up to three substituents independently selected from hydroxy (not on C1 of an alkoxy group, and excluding geminal disubstitution), oxo, trifluoromethyl, cyano, nitro, (1–4C)alkoxy, (2–4C)alkanoyloxy, hydroxyimino, (1–4C)alkoxyimino, (1–4C)alkylS(O)$_q$— (q is 0, 1 or 2), (1–4C)alkylSO$_2$—NRv—, (1–4C)alkoxycarbonyl, —CONRcRv, and —NRcRv (not on C1 of an alkoxy group, and excluding geminal disubstitution); wherein Rv is hydrogen or (1–4C)alkyl and Rc is as hereinbefore defined;

or $R^{4h}$ is selected from one of the groups in (TAaa) to (TAac) below, or (where appropriate) one of $R^{4h}$ and $R^{5h}$ is selected from the above list of $R^{4h}$ and $R^{5h}$ values, and the other is selected from one of the groups in (TAaa) to (TAac) below:—

(TAaa) a group of the formula (TAaa1)

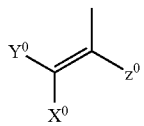
(TAaa1)

wherein $Z^0$ is hydrogen or (1–4C)alkyl;
$X^0$ and $Y^0$ are independently selected from hydrogen, (1–4C)alkyl, (1–4C)alkoxycarbonyl, halo, cyano, nitro, (1–4C)alkylS(O)$_q$— (q is 0, 1 or 2), RvRwNSO$_2$—, trifluoromethyl, pentafluoroethyl, (1–4C)alkanoyl and —CONRvRw [wherein Rv is hydrogen or (1–4C)alkyl; Rw is hydrogen or (1–4C)alkyl]; or
one of $X^0$ and $Y^0$ is selected from the above list of $X^0$ and $Y^0$ values, and the other is selected from phenyl, phenylcarbonyl, —S(O)$_q$-phenyl (q is 0, 1 or 2), N-(phenyl)carbamoyl, phenylaminosulfonyl, AR2, (AR2)-CO—, (AR2)-S(O)$_q$— (q is 0, 1 or 2), N-(AR2)carbamoyl and (AR2)aminosulfonyl; wherein any phenyl group in (TAaa) may be optionally substituted by up to three substituents independently selected from (1–4C) alkyl, cyano, trifluoromethyl, nitro, halo and (1–4C)alkylsulfonyl;
(TAab) an acetylene of the formula -≡-H or -≡-(1–4C)alkyl;
(TAac) —$X^1$—$Y^1$-AR2, —$X^1$—$Y^1$-AR2a, —$X^1$—$Y^1$-AR2b, —$X^1$—$Y^1$-AR3, —$X^1$—$Y^1$-AR3a or —$X^1$—$Y^1$-AR3b;

wherein $X^1$ is a direct bond or —CH(OH)— and
$Y^1$ is —(CH$_2$)$_m$—, —(CH$_2$)$_n$—NH—(CH$_2$)$_m$—, —CO—(CH$_2$)$_m$—, —CONH—(CH$_2$)$_m$—, —C(=S)NH—(CH$_2$)$_m$— or —C(=O)O—(CH$_2$)$_m$—;

or wherein $X^1$ is —(CH$_2$)$_n$— or —CH(Me)—(CH$_2$)$_m$— and
$Y^1$ is —(CH$_2$)$_m$—NH—(CH$_2$)$_m$—, —CO—(CH$_2$)$_m$—, —CONH—(CH$_2$)$_m$—, —C(=S)NH—(CH$_2$)$_m$—, —C(=O)O—(CH$_2$)$_m$— or —S(O)$_q$—(CH$_2$)$_m$—;

or wherein $X^1$ is —CH$_2$O—, —CH$_2$NH— or —CH$_2$N((1–4C)alkyl)- and
$Y^1$ is —CO—(CH$_2$)$_m$—, —CONH—(CH$_2$)$_m$— or —C(=S)NH—(CH$_2$)$_m$—; and additionally $Y^1$ is —SO$_2$— when $X^1$ is —CH$_2$NH— or —CH$_2$N((1–4C)alkyl)-, and $Y^1$ is —(CH$_2$)$_m$— when $X^1$ is —CH$_2$O— or —CH$_2$N((1–4C)alkyl)-; wherein n is 1, 2 or 3; m is 0, 1, 2 or 3 and q is 0, 1 or 2; and when $Y^1$ is —(CH$_2$)$_m$—NH—(CH$_2$)$_m$— each m is independently selected from 0, 1, 2 or 3.

It is to be understood that when a value for —$X^1$— is a two-atom link and is written, for example, as —CH$_2$NH— it is the left hand part (—CH$_2$— here) which is bonded to the group of formula (TAa1) to (TAa6) and the right hand part (—NH— here) which is bonded to —$Y^1$— in the definition in (TAac). Similarly, when —$Y^1$— is a two-atom link and is written, for example, as —COHN— it is the left hand part of —$Y^1$—(—CO— here) which is bonded to the right hand part of —$X^1$—, and the right hand part of —$Y^1$—(—NH— here) which is bonded to the AR2, AR2a, AR2b, AR3, AR3a or AR3b moiety in the definition in (TAac).

Preferably $R^{6h}$ is hydrogen or (1–4C)alkyl, and $R^{4h}$ and $R^{5h}$ are independently selected from hydrogen, cyano, (1–4C)alkoxycarbonyl, —CONRvRw, hydroxy(1–4C)alkyl, NRvRw(1–4C)alkyl, —NRcRv(1–4C)alkyl; wherein Rv is hydrogen or (1–4C)alkyl; Rw is hydrogen or (1–4C)alkyl}; Rc is as hereinbefore defined.

More preferably, $R^{5h}$ and $R^{6h}$ are hydrogen and $R^{4h}$ is selected from cyano, (1–4C)alkoxycarbonyl, —CONRcRv (preferably with Rc as hydrogen or (1–4C)alkyl), hydroxy-(1–4C)alkyl and —NRcRv(1–4C)alkyl; wherein Rv is hydrogen or (1–4C)alkyl and Rc is preferably (Rc2) as hereinbefore defined (especially wherein $R^{13}$ is (Rc2c) as hereinbefore defined).

When $R^{4h}$ and $R^{5h}$ are independently selected from optionally substituted (as defined) (1–4C)alkyl, preferably there are one or two substituents, most especially just one substituent; and when the optional substituent is —CONRcRv or —NRcRv, Rc is preferably hydrogen, (1–4C)alkyl or (1–4C)alkanoyl.

The above preferred values of (TAa) are particularly preferred when present in Q1 or Q2, especially Q1. Most preferable is (TAa1) with preferable $R^{4h}$ substituents as hereinbefore defined.

In this specification, for
(TAf) When T is an optionally substituted N-linked (fully unsaturated) 5-membered heteroaryl ring system containing 1, 2 or 3 nitrogen atoms, it is preferably selected from a group of formula (TAf1) to (TAf6) below (particularly (TAf1), (TAf2), (TAf4) and (TAf5), and especially (TAf1) and/or (TAf2)). The above preferred values of (TAf) are particularly preferred when present in Q1 or Q2, especially Q1.

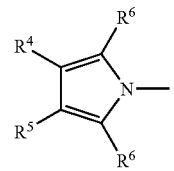
(TAf1)

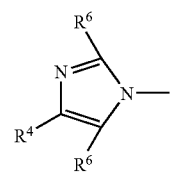
(TAf2)

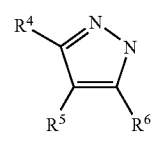
(TAf3)

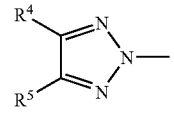
(TAf4)

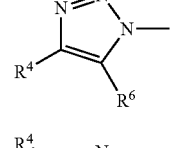
(TAf5)

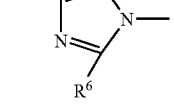
(TAf6)

wherein:

R$^6$ is selected (independently where appropriate) from hydrogen, (1–4C)alkyl, (1–4C)alkoxycarbonyl, (1–4C)alkanoyl, carbamoyl and cyano;

R$^4$ and R$^5$ are independently selected from hydrogen, halo, trifluoromethyl, cyano, nitro, (1–4C)alkoxy, (1–4C)alkylS(O)$_q$— (q is 0, 1 or 2), (1–4C)alkanoyl, (1–4C)alkoxycarbonyl, benzyloxy-(1–4C)alkyl, (2–4C)alkanoylamino, —CONRcRv and —NRcRv wherein any (1–4C)alkyl group contained in the preceding values for R$^4$ and R$^5$ is optionally substituted by up to three substituents independently selected from hydroxy (not on C1 of an alkoxy group, and excluding geminal disubstitution), oxo, trifluoromethyl, cyano, nitro, (1–4C)alkoxy, (2–4C)alkanoyloxy, hydroxyimino, (1–4C)alkoxyimino, (1–4C)alkylS(O)$_q$— (q is 0, 1 or 2), (1–4C)alkylSO$_2$—NRv—, (1–4C)alkoxycarbonyl, —CONRcRv, and —NRcRv (not on C1 of an alkoxy group, and excluding geminal disubstitution); wherein Rv is hydrogen or (1–4C)alkyl and Rc is as hereinbefore defined;

R$^4$ and R$^5$ may further be independently selected from (1–4C)alkyl {optionally substituted by up to three substituents independently selected from hydroxy (excluding geminal disubstitution), oxo, trifluoromethyl, cyano, nitro, (1–4C)alkoxy, (2–4C)alkanoyloxy, hydroxyimino, (1–4C)alkoxyimino, (1–4C)alkylS(O)$_q$— (q is 0, 1 or 2), (1–4C)alkylSO$_2$—NRv—, (1–4C)alkoxycarbonyl, —CONRcRv, and —NRcRv (excluding geminal disubstitution); wherein Rv is hydrogen or (1–4C)alkyl}; Rc is as hereinbefore defined; and wherein any (1–4C)alkyl group contained in the immediately preceding optional substituents (when R$^4$ and R$^5$ are independently (1–4C)alkyl) is itself optionally substituted by up to three substituents independently selected from hydroxy (not on C1 of an alkoxy group, and excluding geminal disubstitution), oxo, trifluoromethyl, cyano, nitro, (1–4C)alkoxy, (2–4C)alkanoyloxy, hydroxyimino, (1–4C)alkoxyimino, (1–4C)alkylS(O)$_q$— (q is 0, 1 or 2), (1–4C)alkylSO$_2$—NRv—, (1–4C)alkoxycarbonyl, —CONRcRv, and —NRcRv (not on C1 of an alkoxy group, and excluding geminal disubstitution); wherein Rv is hydrogen or (1–4C)alkyl and Rc is as hereinbefore defined;

or R$^4$ is selected from one of the groups in (TAfa) to (TAfc) below, or (where appropriate) one of R$^4$ and R$^5$ is selected from the above list of R$^4$ and R$^5$ values, and the other is selected from one of the groups in (TAfa) to (TAfc) below:—

(TAfa) a group of the formula (TAfa1)

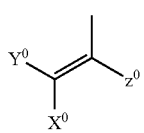

(TAfa1)

wherein Z$^0$ is hydrogen or (1–4C)alkyl;

X$^0$ and Y$^0$ are independently selected from hydrogen, (1–4C)alkyl, (1–4C)alkoxycarbonyl, halo, cyano, nitro, (1–4C)alkylS(O)$_q$— (q is 0, 1 or 2), RvRwNSO$_2$—, trifluoromethyl, pentafluoroethyl, (1–4C)alkanoyl and —CONRvRw [wherein Rv is hydrogen or (1–4C)alkyl; Rw is hydrogen or (1–4C)alkyl]; or one of X$^0$ and Y$^0$ is selected from the above list of X$^0$ and Y$^0$ values, and the other is selected from phenyl, phenylcarbonyl, —S(O)$_q$-phenyl (q is 0, 1 or 2), N-(phenyl)carbamoyl, phenylaminosulfonyl, AR2, (AR2)-CO-, (AR2)—S(O)$_q$— (q is 0, 1 or 2), N-(AR2)carbamoyl and (AR2)aminosulfonyl; wherein any phenyl group in (TAfa) may be optionally substituted by up to three substituents independently selected from (1–4C)alkyl, cyano, trifluoromethyl, nitro, halo and (1–4C)alkylsulfonyl;

(TAfb) an acetylene of the formula -≡-H or -≡-(1–4C)alkyl;

(TAfc) —X$^1$—Y$^1$-AR2, —X$^1$—Y$^1$-AR2a, —X$^1$—Y$^1$-AR2b, —X$^1$—Y$^1$-AR3, —X$^1$—Y$^1$-AR3a or —X$^1$—Y$^1$-AR3b;

wherein X$^1$ is a direct bond or —CH(OH)— and
Y$^1$ is —(CH$_2$)$_m$—, —(CH$_2$)$_n$—NH—(CH$_2$)$_m$—, —CO—(CH$_2$)$_m$—, —COHN—(CH$_2$)$_m$—, —C(=S)NH—(CH$_2$)$_m$— or —C(=O)O—(CH$_2$)$_m$;

or wherein X$^1$ is —(CH$_2$)$_n$— or —CH(Me)—(CH$_2$)$_m$— and
Y$^1$ is —(CH$_2$)$_m$—NH—(CH$_2$)$_m$—, —CO—(CH$_2$)$_m$—, —CONH—(CH$_2$)$_m$—, —C(=S)NH—(CH$_2$)$_m$—, —C(=O)O—(CH$_2$)$_m$— or —S(O)$_q$—(CH$_2$)$_m$—;

or wherein X$^1$ is —CH$_2$O—, —CH$_2$NH— or —CH$_2$N((1–4C)alkyl)- and
Y$^1$ is —CO—(CH$_2$)$_m$—, —CONH—(CH$_2$)$_m$— or —C(=S)NH—(CH$_2$)$_m$—; and additonally Y$^1$ is —SO$_2$— when X$^1$ is —CH$_2$NH— or —CH$_2$N((1–4C)alkyl)-, and Y$^1$ is —(CH$_2$)$_m$— when X$^1$ is —CH$_2$O— or —CH$_2$N((1–4C)alkyl)-; wherein n is 1, 2 or 3; m is 0, 1, 2 or 3 and q is 0, 1 or 2; and when Y$^1$ is —(CH$_2$)$_m$—NH—(CH$_2$)$_m$— each m is independently selected from 0, 1, 2 or 3.

It is to be understood that when a value for —X$^1$— is a two-atom link and is written, for example, as —CH$_2$NH— it is the left hand part (—CH$_2$— here) which is bonded to the group of formula (TAf1) to (TAf6) and the right hand part (—NH— here) which is bonded to —Y$^1$— in the definition in (TAfc). Similarly, when —Y$^1$— is a two-atom link and is written, for example, as —CONH— it is the left hand part of —Y$^1$—(—CO— here) which is bonded to the right hand part of —X$^1$—, and the right hand part of —Y$^1$—(—NH— here) which is bonded to the AR2, AR2a, AR2b, AR3, AR3a or AR3b moiety in the definition in (TAfc).

Preferably R$^6$ is hydrogen or (1–4C)alkyl, and R$^4$ and R$^5$ are independently selected from hydrogen, (1–4C)alkyl or one of R$^4$ and R$^5$ is selected from group (TAfa). Most preferable is (TAf2) with such preferable substituents.

In this specification, for (TAg) When T is a carbon linked tropol-3-one or tropol-4-one, optionally substituted in a position not adjacent to the linking position (TAg), it is preferably selected from a group of formula (TAg1), (TAg2) or (TAg3). The above preferred values of (TAg) are particularly preferred when present in Q1 or Q2, especially Q1.

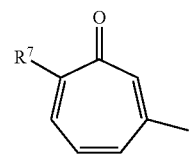

(TAg1)

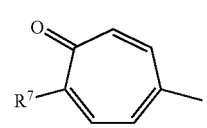

(TAg2)

-continued (TAg3)

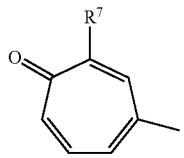

wherein R⁷ is selected from (TAga) hydrogen, (1–4C)alkyl {optionally substituted by one or two substituents (excluding geminal disubstitution) independently selected from fluoro, hydroxy, (1–4C) alkoxy and —NRvRw]}; or (TAgb) R⁸—O—, R⁸—S—, R⁸—NH— or R⁸R⁸—N—;

wherein R⁸ is selected (independently where appropriate) from hydrogen, (1–4C)alkyl or (3–8C)cycloalkyl {both optionally substituted by one or two substituents (excluding geminal disubstitution) independently selected from hydroxy, (1–4C)alkoxy, (1–4C)alkoxycarbonyl and —NRvRw}, (2–4C)alkenyl {optionally substituted by one or two —NRvRw substituents}, (1–4C)alkanoyl {optionally substituted by one or two substituents independently selected from —NRvRw and hydroxy}, phenyl-(1–4C)alkyl or pyridyl-(1–4C)alkyl {the phenyl and pyridyl (preferably pyridin-4-yl) rings being optionally substituted by one or two —NRvRw substituents}; or (TAgc) morpholino, thiomorpholino, pyrrolidino {optionally independently substituted in the 3- and/or 4-positions by (1–4C)alkyl}, piperidino substituted in the 4-position by R⁹—, R⁹—O—, R⁹—S—, R⁹—NH— or R⁹R⁹—N—; wherein R⁹ is selected (independently where appropriate) from hydrogen, (1–4C)alkyl {optionally substituted by one or two (excluding geminal disubstitution) hydroxy, (1–4C)alkoxy, (1–4C)alkoxycarbonyl or —NRvRw} and piperazino {optionally substituted in the 4-position by (1–4C)alkyl, (3–8C)cycloalkyl, (1–4C)alkanoyl, (1–4C) alkoxycarbonyl or (1–4C)alkylsulfonyl, and optionally independently substituted in the 3- and/or 5-positions by (1–4C)alkyl}; wherein Rv is hydrogen or (1–4C)alkyl; Rw is hydrogen or (1–4C)alkyl.

In this specification, for (TC) Preferred values for the optional substituents and groups defined in (TCa) to (TCc) are defined by formulae (TC1) to (TC4):—

(TC1)

(TC2)

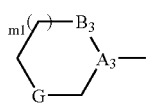

(TC3)

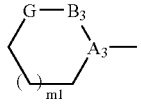

-continued (TC4)

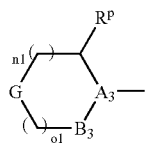

wherein in (TC1): >A₃-B₃- is >C(Rq)—CH(Rr)— or >N—CH₂— and G is —O—, —S—, —SO—, —SO₂— or >N(Rc);

wherein in (TC2): m1 is 0, 1 or 2; >A₃-B₃- is >C=C(Rr)— or >C(Rq)—CH(Rr)— or >N—CH₂— and G is —O—, —S—, —SO—, —SO₂— or >N(Rc);

wherein in (TC3): m1 is 0, 1 or 2; >A₃-B₃- is >C(Rq)—CH (Rr)— (other than when Rq and Rr are both together hydrogen) or >N—CH₂— and G is —O—, —S—, —SO—, —SO₂— or >N(Rc);

wherein in (TC4): n1 is 1 or 2; o1 is 1 or 2 and n1+o1=2 or 3; >A₃-B₃- is >C=C(Rr)— or >C(Rq)—CH(Rr)— or >N—CH₂— and G is —O—, —S—, —SO—, —SO₂— or >N(Rc); Rp is hydrogen, (1–4C)alkyl (other than when such substitution is defined by >A₃-B₃-), hydroxy, (1–4C)alkoxy or (1–4C)alkanoyloxy;

wherein in (TC1), (TC2) and (TC4); m1, n1 and o1 are as defined hereinbefore: >A₃-B₃- is >N-CH₂— and G is >C(R¹¹)(R¹²), >C=O, >C—OH, >C—(1–4C)alkoxy, >C=N—OH, >C=N—(1–4C)alkoxy, >C=N—NH—(1–4C)alkyl, >C=N—N((1–4C)alkyl)₂ (the last two (1–4C) alkyl groups above in G being optionally substituted by hydroxy) or >C=N—N—CO—(1–4C)alkoxy; wherein >represents two single bonds;

Rq is hydrogen, hydroxy, halo, (1–4C)alkyl or (1–4C) alkanoyloxy;

Rr is (independently where appropriate) hydrogen or (1–4C) alkyl;

R¹¹ is hydrogen, (1–4C)alkyl, fluoro(1–4C)alkyl, (1–4C) alkyl-thio-(1–4C)alkyl or hydroxy-(1–4C)alkyl and R¹² is —[C(Rr)(Rr)]ₘ₂—N(Rr)(Rc) wherein m2 is 0, 1 or 2; and, other than the ring substitution defined by G, >A₃-B₃- and Rp, each ring system may be optionally further substituted on a carbon atom not adjacent to the link at >A₃- by up to two substituents independently selected from (1–4C)alkyl, fluoro(1–4C)alkyl (including trifluoromethyl), (1–4C)alkyl-thio-(1–4C)alkyl, hydroxy-(1–4C)alkyl, amino, amino-(1–4C)alkyl, (1–4C)alkanoylamino, (1–4C)alkanoylamino-(1–4C)alkyl, carboxy, (1–4C)alkoxycarbonyl, ARc-oxymethyl, ARc-thiomethyl, oxo (=O) (other than when G is >N-Rc and Rc is group (Rc2) defined hereinbefore) or independently selected from Rc; and also hydroxy or halo (the last two optional substituents only when G is —O— or —S—);

wherein ARc is selected from AR1, AR2, AR2a, AR2b, CY1 and CY2 defined herein; Rc is selected from groups (Rc1) to (Rc5) defined hereinbefore.

For the avoidance of doubt, ( )ₘ₁, ( )ₙ₁ and ( )ₒ₁ indicate (—CH₂—)ₘ₁, (—CH₂—)ₙ₁ and (—CH₂—)ₒ₁ respectively (optionally substituted as described above).

In the above definition of (TC1) to (TC4), in an alternative embodiment >A₃-B₃- is not >N—CH₂— in (TC1) to (TC3).

In the above definition of (TC1) to (TC4) and of the further optional substituents:—

(i) ARc is preferably AR2, and the further optional substituents are preferably not selected from the values listed for Rc.

(ii) A preferred value for G is >N(Rc) or >C($R^{11}$)($R^{12}$). Also preferred is G as O or S, particularly in (TC4) when Rp is hydrogen.

(iii) Preferred is (TC4) as piperazinyl, morpholino or thiomorpholino or as tetrahydropyridin-4-yl.

(iv) >$A_3$-$B_3$- is preferably >C(Rq)—CH(Rr)— in (TC1) to (TC3).

Particularly preferred values for the optional substituents and groups defined in (TCa) to (TCc), and (TC1) to (TC4) are contained in the following definitions (TC5) to (TC11):—

(TC5)

(TC6)

(TC7)

(TC8)

(TC9)

(TC10)

(TC11)

wherein Rc has any of the values listed hereinbefore or hereinafter.

Especially preferred are (TC5), (TC6), (TC7) and (TC9), most especially (TC5) in which Rc has any of the values listed hereinbefore or hereinafter (especially $R^{13}$CO— with the preferable $R^{13}$ values given hereinafter). In (TC5) Rc is preferably selected from the group (Rc2), especially $R^{13}$CO— with the preferable $R^{13}$ values given hereinafter. In (TC7) Rc is preferably selected from group (Rc3) or (Rc4).

In this specification, for (TC) Further preferred values for the optional substituents and groups defined in (TC) are defined by formulae (TC12) and (TC13):—

(TC12)

(TC13)

wherein:

in (TC12), ( )$o_1$ is 0 or 1 and represents a chain of carbon atoms (optionally substituted as defined for AR1) of length $o_1$ and M is a bond joining the adjacent carbon atoms, or M represents one or two carbon atoms, and defines a 4- to 7-membered monocyclic ring, which ring may optionally have one of (i) one double bond between any two ring carbon atoms; or (ii) a C1–C3 bridge connecting any two appropriate, non-adjacent ring carbon atoms, which bridge may optionally contain one heteroatom selected from oxygen or >NRc; or (iii) a C2–C5 cyclic moiety including a ring carbon atom to define a spiro C2–C5 ring system, which ring may optionally contain one heteroatom selected from oxygen or >NRc; or (iv) a C1–C4 bridge connecting adjacent carbon atoms to define a fused ring, wherein a C2–C4 bridge may optionally contain one heteroatom selected from oxygen or >NRc; wherein Rc is as defined hereinbefore;

wherein in (TC13), ( )$n_1$ and ( )$o_1$ are independently 0, 1 or 2 and represent chains of carbon atoms (optionally substituted as defined for AR1) of length $n_1$ and $o_1$ respectively, and define a 4- to 8-membered monocyclic ring, which ring may optionally have one of (i) a C1–C3 bridge connecting any two appropriate, non-adjacent ring carbon atoms, which bridge contains one heteroatom selected from oxygen or >NRc; or (ii) a C2–C5 cyclic moiety including a ring carbon atom to define a spiro C2–C5 ring system, which ring may optionally contain one heteroatom selected from oxygen or >NRc; or (iii) a C1–C4 bridge connecting adjacent carbon atoms to define a fused ring, wherein a C2–C4 bridge may optionally contain one heteroatom selected from oxygen or >NRc; wherein Rc is as defined hereinbefore; and wherein in (TC12) and (TC13), $X_{1m}$ and $X_{2m}$ taken together represent $R_{2s}$—(E)$_{ms}$—N=; or $X_{1m}$ is O= and $X_{2m}$ is $R_{2s}$—(E)$_{ms}$—N—, and vice versa;

wherein E is an electron withdrawing group selected from —$SO_2$—, —CO—, —O—CO—, —CO—O—, —CS—, —CON($R_s$)—, —$SO_2$N($R_s$)—, or E may represent a group of the formula $R_{3s}$—C(=N—O—$R_{3s}$)—C(=O)—, wherein $R_3$, is H or as defined in $R_2$, at (i) below;

or, when E is —CON($R_s$)— or —$SO_2$N($R_s$)—, $R_{2s}$ and $R_s$ may link together to form a carbon chain which defines a 5- or 6-membered saturated, unsaturated or partially unsaturated ring linked via the N atom in E, which ring is optionally further substituted by an oxo substituent, and which ring may be optionally fused with a phenyl group to form a benzo-fused system, wherein the phenyl group is optionally substituted by up to three substituents independently selected from halo, cyano, (1–4C)alkyl and (1–4C)alkoxy;
ms is 0 or 1;
$R_2$, and R, are independently selected from:
(i) hydrogen (except where E is —$SO_2$— or —O—CO—), or (1–6C)alkyl {optionally substituted by one or more (1–4C)alkanoyl groups (including geminal disubstitution) and/or optionally monosubstituted by cyano, cyanoimino, (1–4C)alkoxy, trifluoromethyl, (1–4C)alkoxycarbonyl, phenyl (optionally substituted as defined for AR1 herein), optionally substituted heteroaryl group of the formula AR2, AR2a, AR2b, AR3, AR3a, AR3b, AR4, AR4a or CY1 all as defined (and optionally substituted as defined) herein, (1–4C)alkylS(O)$_q$— (q is 0, 1 or 2); and/or (with the proviso that where $R_2$, is —$SO_2$ or —O—CO— not on the first carbon atom of the (1–6C) alkyl chain) optionally substituted by one or more groups (including geminal disubstitution) each independently selected from hydroxy and fluoro, and/or optionally further substituted, by no more than one of each of, oxo, —NRvRw [wherein Rv is hydrogen or (1–4C)alkyl; Rw is hydrogen or (1–4C)alkyl], (1–6C)alkanoylamino, (1–4C)alkoxycarbonylamino, N—(1–4C)alkyl-N—(1–6C)alkanoylamino, (1–4C)alkylS(O)$_p$NH— or (1–4C)alkylS(O)$_p$-((1–4C)alkyl)N— (p is 1 or 2)}; or
(ii) an optionally substituted aryl or optionally substituted heteroaryl group of the formula AR1, AR2, AR2a, AR2b, AR3, AR3a, AR3b, AR4, AR4a or CY1 all as defined (and optionally substituted as defined) herein;

or (where ms is 0 only);
(iii) cyano, —CO—NRvRw, —CO—NRvRw', —$SO_2$—NRvRw, —$SO_2$—NRvRw' [wherein Rv is hydrogen or (1–4C)alkyl; Rw is hydrogen or (1–4C)alkyl; Rw' is phenyl (optionally substituted as defined for AR1 herein), or a heteroaryl group selected from AR2, AR2a, AR2b, AR3, AR3a, AR3b, AR4, AR4a (optionally substituted as defined herein)], (1–4C)alkoxycarbonyl, trifluoromethyl, ethenyl, 2-(1–4C)alkylethenyl, 2-cyanoethenyl, 2-cyano-2-((1–4C)alkyl)ethenyl, 2-nitroethenyl, 2-nitro-2-((1–4C) alkyl)ethenyl, 2-((1–4C)alkylaminocarbonyl)ethenyl, 2-((1–4C)alkoxycarbonyl)ethenyl, 2-(AR1)ethenyl, 2-(AR2)ethenyl, or 2-(AR2a)ethenyl.

In (TC12), when the ring has an optional double bond between any two ring carbon atoms, the ring is preferably linked via an $sp^2$ carbon atom of the double bond.

Preferably (TC12) is (TC12a) or (TC12b), and preferably (TC13) is (TC13a):—

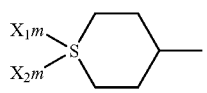
(TC12a)

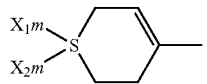
(TC12b)

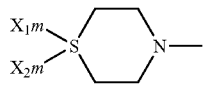
(TC13a)

In this specification, for
(TE) In (TE1) to (TE3), preferably $n_1=o_1$ & $n_{1'}=o_{1'}$ (most preferably all are 1); $p_1=p_{1'}$ (most preferably both are 0); and further preferred values for the optional substituents and groups defined in (TE) are defined by formulae (TE1a, b), (TE2a) and (TE3a):—

(TE1a)

(TE1b)

(TE2a)

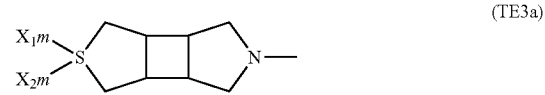
(TE3a)

wherein $X_{1m}$ and $X_{2m}$ are as defined for the formulae (TC12) and (TC13) above.

In this specification, especially for both the further preferred values for the optional substituents and groups defined in (TC) [as defined by formulae (TC12) and (TC13) above]; and for the further preferred values for the optional substituents and groups defined in (TE) [as defined by formulae (TE1a, b), (TE2a) and (TE3a) above]:—

Preferably $X_{1m}$ is O═ and $X_{2m}$ is $R_{2s}$—(E)$_{ms}$—N—, and vice versa.

When ms is 0, $R_{2s}$ is preferably selected from:
(i) hydrogen, a (1–6C)alkyl group {optionally monosubstituted by (1–4C)alkanoyl group, cyano, cyano-imino, (1–4C)alkoxy, trifluoromethyl, (1–4C)alkoxycarbonyl, phenyl (optionally substituted as for AR1 defined herein), optionally substituted heteroaryl group of the formula AR2, AR2a, AR2b, AR3, AR3a, AR3b, AR4, AR4a or CY1 all as defined (and optionally substituted as defined) herein, (1–4C)alkylS(O)$_q$— (q is 0, 1 or 2); or optionally substituted by one or more fluoro groups (including geminal disubstitution); or optionally substituted by one or more hydroxy groups (excluding geminal disubstitution), and/or optionally further substituted, by no more than one of each of, oxo, —NRvRw [wherein Rv is hydrogen or (1–4C)alkyl; Rw is hydrogen or (1–4C) alkyl], (1–6C)alkanoylamino, (1–4C)alkoxycarbonylamino, N—(1–4C)alkyl-N—(1–6C)alkanoylamino, (1–4C)alkylS(O)$_p$NH— or (1–4C)alkylS(O)$_p$—((1–4C) alkyl)N— (p is 1 or 2)}; or
(ii) an optionally substituted aryl or optionally substituted heteroaryl group of the formula AR1, AR2, AR2a, AR2b, AR3, AR3a, AR3b, AR4, AR4a or CY1 all as defined (and optionally substituted as defined) herein; or
(iii) cyano, —CO—NRvRw, —CO—NRvRw', —$SO_2$—NRvRw, —$SO_2$—NRvRw' [wherein Rv is hydrogen or (1–4C)alkyl; Rw is hydrogen or (1–4C)alkyl; Rw' is phenyl (optionally substituted as for AR1 defined herein), or a heteroaryl group selected from AR2, AR2a, AR2b, AR3, AR3a, AR3b, AR4, AR4a (optionally substituted as defined herein)], (1–4C)alkoxycarbonyl, trifluoromethyl.

When ms is 0, $R_2$, is most preferably selected from:
(i) hydrogen, (1–6C)alkyl {optionally monosubstituted by (1–4C)alkoxy, trifluoromethyl, (1–4C)alkylS(O)$_q$— (q is 0, 1 or 2); or optionally substituted by one or more fluoro-groups (including geminal disubstitution); or optionally substituted by one or more hydroxy groups (excluding geminal disubstitution)}; or
(iii) —CO—NRvRw [wherein Rv is hydrogen or (1–4C) alkyl; Rw is hydrogen or (1–4C)alkyl], —CO—NRvRw' [wherein Rv is hydrogen or (1–4C)alkyl; Rw' is phenyl (optionally substituted as for AR1 defined herein)], (1–4C)alkoxycarbonyl.

When ms is 1, E is preferably —CO— or —SO$_2$— and R$_2$, is preferably selected from:
(i) (1–6C)alkyl {optionally monosubstituted by cyano, cyano-imino, (1–4C)alkoxy, trifluoromethyl, (1–4C) alkoxycarbonyl, phenyl (optionally substituted as for AR1 defined herein), optionally substituted heteroaryl group of the formula AR2, AR2a, AR2b, AR3, AR3a, AR3b, AR4, AR4a or CY1 all as defined (and optionally substituted as defined) herein, (1–4C)alkylS(O)$_q$— (q is 0, 1 or 2); and/or (with the proviso that where R$_2$, is —SO$_2$— or —O—CO— not on the first carbon atom of the (1–6C) alkyl chain) optionally substituted by one or more groups (including geminal disubstitution) each independently selected from hydroxy and fluoro, and/or optionally monosubstituted by —NRvRw [wherein Rv is hydrogen or (1–4C)alkyl; Rw is hydrogen or (1–4C)alkyl], (1–6C) alkanoylamino, (1–4C)alkoxycarbonylamino, N—(1–4C)alkyl-N—(1–6C)alkanoylamino, (1–4C) alkylS(O)$_p$NH— or (1–4C)alkylS(O)$_p$—((1–4C)alkyl) N— (p is 1 or 2)}; or
(ii) an optionally substituted aryl or heteroaryl group of the formula AR1, AR2, AR2a, AR2b, AR3, AR3a, AR3b, AR4, AR4a or CY1 all as defined (and optionally substituted as defined) herein.

When ms is 1, E is preferably —CO— or —SO$_2$— and R$_2$, is most preferably selected from:
(i) (1–6C)alkyl {optionally monosubstituted by (1–4C) alkoxy, trifluoromethyl, (1–4C)alkylS(O)$_q$— (q is 0, 1 or 2); or optionally substituted by one or more fluoro groups (including geminal disubstitution); or optionally substituted by one or more hydroxy groups (excluding geminal disubstitution)}, (1–6C)alkanoylamino, (1–4C)alkoxycarbonylamino.

In (TE) and (TC13), where ( )n$_1$, ( )o$_1$, ( )n$_{1'}$, ( )o$_{1'}$, ( )p$_1$ and ( )p$_{1'}$ represents chains of carbon atoms optionally substituted as defined for AR1 herein, preferable optional substituents are selected from (preferably one of) hydroxy, trifluoromethyl, (1–4C)alkyl S(O)$_q$— (q is 0, 1 or 2), (1–4C) alkoxy, (1–4C)alkoxycarbonyl, cyano, nitro, (1–4C)al-kanoylamino, —CONRvRw or —NRvRw [wherein Rv is hydrogen or (1–4C)alkyl; Rw is hydrogen or (1–4C)alkyl]. Most preferably, ( )n$_1$, ( )o$_1$, ( )n$_{1'}$, ( )o$_{1'}$, ( )p$_1$ and ( )p$_{1'}$ represent unsubstituted chains of carbon atoms.

The above preferred values of (TCa) to (TCc) and (TE) are particularly preferred when present in Q1 or Q2, especially Q1.

In this specification, for
(TDa) When T is a bicyclic spiro-ring system as defined in (TDa), it is preferably selected from a group of formula (TDa1) to (TDa9). The above preferred values of (TDa) are particularly preferred when present in Q1 or Q2, especially Q1.

wherein;
(i) the A$_4$ linking group is a nitrogen atom or an sp$^3$ or sp$^2$ carbon atom (with the double bond, where appropriate, orientated in either direction); and
(ii) one of the ring carbon atoms at positions marked * and ** is replaced by one of the following groups —NRc—, >CH—NHRc, >CH—NRc—(1–4C)alkyl, >CH—CH$_2$—NHRc, >CH—CH$_2$—NRc—(1–4C)alkyl [wherein a central —CH$_2$— chain link is optionally mono- or di-substituted by (1–4C)alkyl]; with the provisos that positions marked * are not replaced by —NH— in the ring containing the A$_4$ link when A$_4$ is a nitrogen atom or an sp$^2$ carbon atom, and that positions marked * are not replaced by —NH— in the three membered ring in (TDa1), (TDa4) and (TDa5); and (iii) the ring system is optionally (further) substituted on an available ring carbon atom by up to two substituents independently selected from (1–4C)alkyl, fluoro(1–4C)alkyl (including trifluoromethyl), (1–4C)alkyl-thio-(1–4C)alkyl, hydroxy-(1–4C)alkyl, amino, amino-(1–4C)alkyl, (1–4C)alkanoylamino, (1–4C)alkanoylamino-(1–4C)alkyl, carboxy, (1–4C)alkoxycarbonyl, AR2-oxymethyl, AR2-thiomethyl, oxo (═O) (other than when the ring contains an >N—Rc and Rc is group (Rc2)) and also hydroxy or halo;

wherein Rc has any of the values listed hereinbefore or hereinafter.

In this specification, for (TDb) When T is a 7-, 8- or 9-membered bicyclic ring system containing a bridge of 0, 1 or 2 carbon atoms as defined in (TDb), it is preferably selected from a group defined by the ring skeletons shown in formulae (TDb1) to (TDb14):—

7-membered ring skeletons

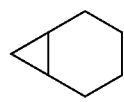

[4,1,0] (TDb1)

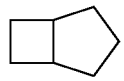

[3,2,0] (TDb2)

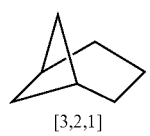

[3,2,1] (TDb3)

[2,2,1] (TDb4)

8-membered ring skeletons

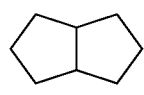

[3,3,0] (TDb5)

[4,2,0] (TDb6)

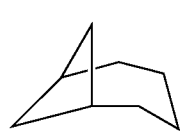

[4,1,1] (TDb7)

-continued

[3,2,1] (TDb8)

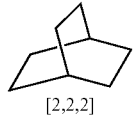

[2,2,2] (TDb9)

9-membered ring skeletons

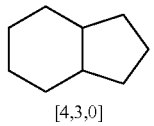

[4,3,0] (TDb10)

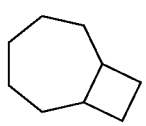

[5,2,0] (TDb11)

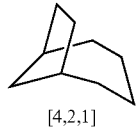

[4,2,1] (TDb12)

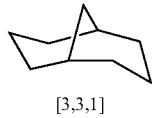

[3,3,1] (TDb13)

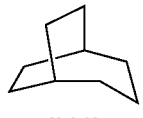

[3,2,2] (TDb14)

wherein;

(i) the ring system contains 0, 1 or 2 ring nitrogen atoms (and optionally a further O or S ring heteroatom), and when present the ring nitrogen, O or S heteroatom/s are at any position other than as part of the 3-membered ring in (TDb1);

(ii) the ring system is linked via a ring nitrogen atom or a ring $sp^3$ or $sp^2$ carbon atom (with the double bond, where appropriate, orientated in either direction) from any position in either ring [other than from a bridgehead position or from an $sp^2$ carbon atom in the 4-membered ring in (TDb2), (TDb6) and (TDb11)];

(iii) one of the ring carbon atoms at a position not adjacent to the linking position, is replaced (other than when the ring contains an O or S heteroatom) by one of the following groups —NRc— [not at a bridgehead position], >C(H)—NHRc, >C(H)—NRc—(1–4C)alkyl, >C(H)—CH₂—NHRc, >C(H)—CH₂—NRc—(1–4C)alkyl [wherein the hydrogen atom shown in brackets is not present when the replacement is made at a bridgehead position and wherein a central —CH₂— chain link is optionally mono- or di-substituted by (1–4C)alkyl]; with the proviso that when the ring system is linked via a ring nitrogen atom or an sp² carbon atom any replacement of a ring carbon atom by —NRc—, O or S is at least two carbon atoms away from the linking position; and (iv) the ring system is optionally (further) substituted on an available ring carbon atom as for the bicyclic spiro-ring systems described in (TDa); wherein Rc has any of the values listed hereinbefore or hereinafter.

It will be appreciated that unstable anti-Bredt compounds are not contemplated in this definition (i.e. compounds with stuctures (TDb3), (TDb4), (TDb7), (TDb8), (TDb9), (TDb12), (TDb13) and (TDb14) in which an sp² carbon atom is directed towards a bridgehead position).

Particularly preferred values of (TDb) are the following structures of formula (TDb4), (TDb8) and/or (TDb9); wherein Rc has any of the values listed hereinbefore or hereinafter.

The above preferred values of (TDb) are particularly preferred when present in Q1 or Q2, especially Q1.

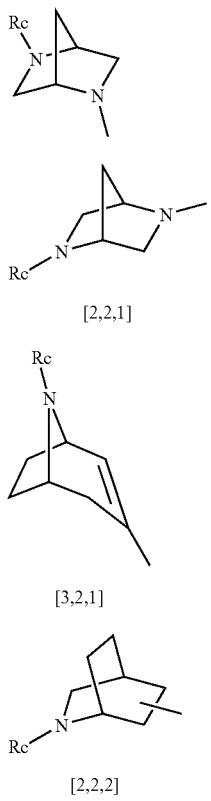

[2,2,1] (TDb4a & b)

[3,2,1] (TDb8)

[2,2,2] (TDb9)

In this specification the term 'alkyl' includes straight chained and branched structures. For example, (1–6C)alkyl includes propyl, isopropyl and tert-butyl. However, references to individual alkyl groups such as "propyl" are specific for the straight chained version only, and references to individual branched chain alkyl groups such as "isopropyl" are specific for the branched chain version only. A similar convention applies to other radicals, for example halo(1–4C)alkyl includes 1-bromoethyl and 2-bromoethyl.

There follow particular and suitable values for certain substituents and groups referred to in this specification. These values may be used where appropriate with any of the definitions and embodiments disclosed hereinbefore, or hereinafter.

Examples of (1–4C)alkyl and (1–5C)alkyl include methyl, ethyl, propyl, isopropyl and t-butyl; examples of (1–6C)alkyl include methyl, ethyl, propyl, isopropyl, t-butyl, pentyl and hexyl; examples of (1–10C)alkyl include methyl, ethyl, propyl, isopropyl, pentyl, hexyl, heptyl, octyl and nonyl; examples of (1–4C)alkanoylamino-(1–4C)alkyl include formamidomethyl, acetamidomethyl and acetamidoethyl; examples of hydroxy(1–4C)alkyl and hydroxy (1–6C)alkyl include hydroxymethyl, 1-hydroxyethyl, 2-hydroxyethyl and 3-hydroxypropyl; examples of (1–4C) alkoxycarbonyl include methoxycarbonyl, ethoxycarbonyl and propoxycarbonyl; examples of 2-((1–4C)alkoxycarbonyl)ethenyl include 2-(methoxycarbonyl)ethenyl and 2-(ethoxycarbonyl)ethenyl; examples of 2-cyano-2-((1–4C) alkyl)ethenyl include 2-cyano-2-methylethenyl and 2-cyano-2-ethylethenyl; examples of 2-nitro-2-((1–4C)alkyl) ethenyl include 2-nitro-2-methylethenyl and 2-nitro-2-ethylethenyl; examples of 2-((1–4C)alkylaminocarbonyl) ethenyl include 2-(methylaminocarbonyl)ethenyl and 2-(ethylaminocarbonyl)ethenyl; examples of (2–4C)alkenyl include allyl and vinyl; examples of (2–4C)alkynyl include ethynyl and 2-propynyl; examples of (1–4C)alkanoyl include formyl, acetyl and propionyl; examples of (1–4C) alkoxy include methoxy, ethoxy and propoxy; examples of (1–6C)alkoxy and (1–10C)alkoxy include methoxy, ethoxy, propoxy and pentoxy; examples of (1–4C)alkylthio include methylthio and ethylthio; examples of (1–4C)alkylamino include methylamino, ethylamino and propylamino; examples of di-((1–4C)alkyl)amino include dimethylamino, N-ethyl-N-methylamino, diethylamino, N-methyl-N-propylamino and dipropylamino; examples of halo groups include fluoro, chloro and bromo; examples of (1–4C)alkylsulfonyl include methylsulfonyl and ethylsulfonyl; examples of (1–4C)alkoxy-(1–4C)alkoxy and (1–6C)alkoxy-(1–6C) alkoxy include methoxymethoxy, 2-methoxyethoxy, 2-ethoxyethoxy and 3-methoxypropoxy; examples of (1–4C)alkoxy-(1–4C)alkoxy-(1–4C)alkoxy include 2-(methoxymethoxy)ethoxy, 2-(2-methoxyethoxy)ethoxy; 3-(2-methoxyethoxy)propoxy and 2-(2-ethoxyethoxy) ethoxy; examples of (1–4C)alkylS(O)₂amino include methylsulfonylamino and ethylsulfonylamino; examples of (1–4C)alkanoylamino and (1–6C)alkanoylamino include formamido, acetamido and propionylamino; examples of (1–4C)alkoxycarbonylamino include methoxycarbonylamino and ethoxycarbonylamino; examples of N-(1–4C) alkyl-N-(1–6C)alkanoylamino include N-methylacetamido, N-ethylacetamido and N-methylpropionamido; examples of (1–4C)alkylthiocarbonylamino include MeS—C(=O)—N— and EtS—C(=O)—N—; examples of (1–4C)alkylS (O)$_p$NH— wherein p is 1 or 2 include methylsulfinylamino, methylsulfonylamino, ethylsulfinylamino and ethylsulfonylamino; examples of (1–4C)alkylS(O)$_p$((1–4C)alkyl)N— wherein p is 1 or 2 include methylsulfinylmethylamino, methylsulfonylmethylamino, 2-(ethylsulfinyl)ethylamino and 2-(ethylsulfonyl)ethylamino; examples of fluoro(1–4C) alkylS(O)$_p$NH— wherein p is 1 or 2 include trifluoromethylsulfinylamino and trifluoromethylsulfonylamino; examples of fluoro(1–4C)alkylS(O)$_p$((1–4C)alkyl)NH— wherein p is 1 or 2 include trifluoromethylsulfinylmethylamino and trifluoromethylsulfonylmethylamino; examples of (1–4C)alkoxy(hydroxy)phosphoryl include methoxy(hydroxy)phosphoryl and ethoxy(hydroxy)phosphoryl; examples of di-(1–4C)alkoxyphosphoryl include di-methoxyphosphoryl, di-ethoxyphosphoryl and ethoxy(methoxy)

phosphoryl; examples of (1–4C)alkylS(O)$_q$— wherein q is 0, 1 or 2 include methylthio, ethylthio, methylsulfinyl, ethylsulfinyl, methylsulfonyl and ethylsulfonyl; examples of phenylS(O)$_q$ and naphthylS(O)$_q$— wherein q is 0, 1 or 2 are phenylthio, phenylsulfinyl, phenylsulfonyl and naphthylthio, naphthylsulfinyl and naphthylsulfonyl respectively; examples of benzyloxy-(1–4C)alkyl include benzyloxymethyl and benzyloxyethyl; examples of a (3–4C)alkylene chain are trimethylene or tetramethylene; examples of (1–6C)alkoxy-(1–6C)alkyl include methoxymethyl, ethoxymethyl and 2-methoxyethyl; examples of hydroxy-(2–6C)alkoxy include 2-hydroxyethoxy and 3-hydroxypropoxy; examples of (1–4C)alkylamino-(2–6C)alkoxy include 2-methylaminoethoxy and 2-ethylaminoethoxy; examples of di-(1–4C)alkylamino-(2–6C)alkoxy include 2-dimethylaminoethoxy and 2-diethylaminoethoxy; examples of phenyl(1–4C)alkyl include benzyl and phenethyl; examples of (1–4C)alkylcarbamoyl include methylcarbamoyl and ethylcarbamoyl; examples of di((1–4C)alkyl)carbamoyl include di(methyl)carbamoyl and di(ethyl)carbamoyl; examples of hydroxyimino(1–4C)alkyl include hydroxyiminomethyl, 2-(hydroxyimino)ethyl and 1-(hydroxyimino)ethyl; examples of (1–4C)alkoxyimino-(1–4C)alkyl include methoxyiminomethyl, ethoxyiminomethyl, 1-(methoxyimino) ethyl and 2-(methoxyimino)ethyl; examples of halo(1–4C) alkyl include, halomethyl, 1-haloethyl, 2-haloethyl, and 3-halopropyl; examples of nitro(1–4C)alkyl include nitromethyl, 1-nitroethyl, 2-nitroethyl and 3-nitropropyl; examples of amino(1–4C)alkyl include aminomethyl, 1-aminoethyl, 2-aminoethyl and 3-aminopropyl; examples of cyano(1–4C) alkyl include cyanomethyl, 1-cyanoethyl, 2-cyanoethyl and 3-cyanopropyl; examples of (1–4C)alkanesulfonamido include methanesulfonamido and ethanesulfonamido; examples of (1–4C)alkylaminosulfonyl include methylaminosulfonyl and ethylaminosulfonyl; and examples of di-(1–4C)alkylaminosulfonyl include dimethylaminosulfonyl, diethylaminosulfonyl and N-methyl-N-ethylaminosulfonyl; examples of (1–4C)alkanesulfonyloxy include methylsulfonyloxy, ethylsulfonyloxy and propylsulfonyloxy; examples of (1–4C)alkanoyloxy include acetoxy; examples of (1–4C) alkylaminocarbonyl include methylaminocarbonyl and ethylaminocarbonyl; examples of di((1–4C)alkyl)aminocarbonyl include dimethylaminocarbonyl and diethylaminocarbonyl; examples of (3–6C)cycloalkyl and (3–8C)cycloalkyl include cyclopropyl, cyclobutyl, cyclopentyl and cyclohexyl; examples of (4–7C)cycloalkyl include cyclobutyl, cyclopentyl and cyclohexyl; examples of (3–6C)cycloalkenyl include cyclopentenyl and cyclohexenyl; examples of di(N-(1–4C)alkyl)aminomethylimino include dimethylaminomethylimino and diethylaminomethylimino.

Particular values for AR2 include, for example, for those AR2 containing one heteroatom, furan, pyrrole, thiophene; for those AR2 containing one to four N atoms, pyrazole, imidazole, pyridine, pyrimidine, pyrazine, pyridazine, 1,2,3- & 1,2,4-triazole and tetrazole; for those AR2 containing one N and one O atom, oxazole, isoxazole and oxazine; for those AR2 containing one N and one S atom, thiazole and isothiazole; for those AR2 containing two N atoms and one S atom, 1,2,4- and 1,3,4-thiadiazole.

Particular examples of AR2a include, for example, dihydropyrrole (especially 2,5-dihydropyrrol-4-yl) and tetrahydropyridine (especially 1,2,5,6-tetrahydropyrid-4-yl).

Particular examples of AR2b include, for example, tetrahydrofuran, pyrrolidine, morpholine (preferably morpholino), thiomorpholine (preferably thiomorpholino), piperazine (preferably piperazino), imidazoline and piperidine, 1,3-dioxolan-4-yl, 1,3-dioxan-4-yl, 1,3-dioxan-5-yl and 1,4-dioxan-2-yl.

Particular values for AR3 include, for example, bicyclic benzo-fused systems containing a 5- or 6-membered heteroaryl ring containing one nitrogen atom and optionally 1–3 further heteroatoms chosen from oxygen, sulfur and nitrogen. Specific examples of such ring systems include, for example, indole, benzofuran, benzothiophene, benzimidazole, benzothiazole, benzisothiazole, benzoxazole, benzisoxazole, quinoline, quinoxaline, quinazoline, phthalazine and cinnoline.

Other particular examples of AR3 include 5/5-, 5/6 and 6/6 bicyclic ring systems containing heteroatoms in both of the rings. Specific examples of such ring systems include, for example, purine and naphthyridine.

Further particular examples of AR3 include bicyclic heteroaryl ring systems with at least one bridgehead nitrogen and optionally a further 1–3 heteroatoms chosen from oxygen, sulfur and nitrogen. Specific examples of such ring systems include, for example, 3H-pyrrolo[1,2-a]pyrrole, pyrrolo[2,1-b]thiazole, 1H-imidazo[1,2-a]pyrrole, 1H-imidazo[1,2-a]imidazole, 1H,3H-pyrrolo[1,2-c]oxazole, 1H-imidazo[1,5-a]pyrrole, pyrrolo[1,2-b]isoxazole, imidazo[5,1-b]thiazole, imidazo[2,1-b]thiazole, indolizine, imidazo[1,2-a]pyridine, imidazo[1,5-a]pyridine, pyrazolo[1,5-a]pyridine, pyrrolo[1,2-b]pyridazine, pyrrolo[1,2-c]pyrimidine, pyrrolo[1,2-a]pyrazine, pyrrolo[1,2-a]pyrimidine, pyrido[2,1-c]-s-triazole, s-triazolo[1,5-a]pyridine, imidazo[1,2-c]pyrimidine, imidazo[1,2-a]pyrazine, imidazo[1,2-a]pyrimidine, imidazo[1,5-a]pyrazine, imidazo[1,5-a]pyrimidine, imidazo[1,2-b]-pyridazine, s-triazolo[4,3-a]pyrimidine, imidazo[5,1-b]oxazole and imidazo[2,1-b]oxazole. Other specific examples of such ring systems include, for example, [1H]-pyrrolo[2,1-c]oxazine, [3H]-oxazolo[3,4-a]pyridine, [6H]-pyrrolo[2,1-c]oxazine and pyrido[2,1-c][1,4]oxazine. Other specific examples of 5/5-bicyclic ring systems are imidazooxazole or imidazothiazole, in particular imidazo[5,1-b]thiazole, imidazo[2,1-b]thiazole, imidazo[5,1-b]oxazole or imidazo[2,1-b]oxazole.

Particular examples of AR3a and AR3b include, for example, indoline, 1,3,4,6,9,9a-hexahydropyrido[2,1c][1,4]oxazin-8-yl, 1,2,3,5,8,8a-hexahydroimidazo[1,5a]pyridin-7-yl, 1,5,8,8a-tetrahydrooxazolo[3,4a]pyridin-7-yl, 1,5,6,7,8,8a-hexahydrooxazolo[3,4a]pyridin-7-yl, (7aS)[3H,5H]-1,7a-dihydropyrrolo[1,2c]oxazol-6-yl, (7aS)[5H]-1,2,3,7a-tetrahydropyrrolo[1,2c]imidazol-6-yl, (7aR)[3H,5H]-1,7a-dihydropyrrolo[1,2c]oxazol-6-yl, [3H,5H]-pyrrolo[1,2-c]oxazol-6-yl, [5H]-2,3-dihydropyrrolo[1,2-c]imidazol-6-yl, [3H,5H]-pyrrolo[1,2-c]thiazol-6-yl, [3H,5H]-1,7a-dihydropyrrolo[1,2-c]thiazol-6-yl, [5H]-pyrrolo[1,2-c]imidazol-6-yl, [1H]-3,4,8,8a-tetrahydropyrrolo[2,1-c]oxazin-7-yl, [3H]-1,5,8,8a-tetrahydrooxazolo[3,4-a]pyrid-7-yl, [3H]-5,8-dihydroxazolo[3,4-a]pyrid-7-yl and 5,8-dihydroimidazo[1,5-a]pyrid-7-yl.

Particular values for AR4 include, for example, pyrrolo[a]quinoline, 2,3-pyrroloisoquinoline, pyrrolo[a]isoquinoline, 1H-pyrrolo[1,2-a]benzimidazole, 9H-imidazo[1,2-a]indole, 5H-imidazo[2,1-a]isoindole, 1H-imidazo[3,4-a]indole, imidazo[1,2-a]quinoline, imidazo[2,1-a]isoquinoline, imidazo[1,5-a]quinoline and imidazo[5,1-a]isoquinoline.

The nomenclature used is that found in, for example, "Heterocyclic Compounds (Systems with bridgehead nitrogen), W. L. Mosby (Intercsience Publishers Inc., New York), 1961, Parts 1 and 2.

Where optional substituents are listed such substitution is preferably not geminal disubstitution unless stated otherwise. If not stated elsewhere suitable optional substituents for a particular group are those as stated for similar groups herein.

Suitable substituents on AR1, AR2, AR2a, AR2b, AR3, AR3a, AR3b, AR4, AR4a, CY1 and CY2 are (on an available carbon atom) up to three substituents independently selected from (1–4C)alkyl {optionally substituted by (preferably one) substituents selected independently from hydroxy, trifluoromethyl, (1–4C)alkyl S(O)$_q$— (q is 0, 1 or 2) (this last substituent preferably on AR1 only), (1–4C)alkoxy, (1–4C)alkoxycarbonyl, cyano, nitro, (1–4C)alkanoylamino, —CONRvRw or —NRvRw}, trifluoromethyl, hydroxy, halo, nitro, cyano, thiol, (1–4C)alkoxy, (1–4C)alkanoyloxy, dimethylaminomethyleneaminocarbonyl, di(N-(1–4C)alkyl)aminomethylimino, carboxy, (1–4C)alkoxycarbonyl, (1–4C)alkanoyl, (1–4C)alkylSO$_2$amino, (2–4C)alkenyl {optionally substituted by carboxy or (1–4C)alkoxycarbonyl}, (2–4C)alkynyl, (1–4C)alkanoylamino, oxo (=O), thioxo (=S), (1–4C)alkanoylamino {the (1–4C)alkanoyl group being optionally substituted by hydroxy}, (1–4C)alkyl S(O)$_q$— (q is 0, 1 or 2) {the (1–4C)alkyl group being optionally substituted by one or more groups independently selected from cyano, hydroxy and (1–4C)alkoxy}, —CONRvRw or —NRvRw [wherein Rv is hydrogen or (1–4C)alkyl; Rw is hydrogen or (1–4C)alkyl].

Further suitable substituents on AR1, AR2, AR2a, AR2b, AR3, AR3a, AR3b, AR4, AR4a, CY1 and CY2 (on an available carbon atom), and also on alkyl groups (unless indicated otherwise) are up to three substituents independently selected from trifluoromethoxy, benzoylamino, benzoyl, phenyl {optionally substituted by up to three substituents independently selected from halo, (1–4C)alkoxy or cyano}, furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C)alkoxyimino(1–4C)alkyl, halo-(1–4C)alkyl, (1–4C)alkanesulfonamido, —SO$_2$NRvRw [wherein Rv is hydrogen or (1–4C)alkyl; Rw is hydrogen or (1–4C)alkyl].

Preferable optional substituents on Ar2b as 1,3-dioxolan-4-yl, 1,3-dioxan-4-yl, 1,3-dioxan-5-yl or 1,4-dioxan-2-yl are mono- or disubstitution by substituents independently selected from (1–4C)alkyl (including geminal disubstitution), (1–4C)alkoxy, (1–4C)alkylthio, acetamido, (1–4C)alkanoyl, cyano, trifluoromethyl and phenyl].

Preferable optional substituents on CY1 & CY2 are mono- or disubstitution by substituents independently selected from (1–4C)alkyl (including geminal disubstitution), hydroxy, (1–4C)alkoxy, (1–4C)alkylthio, acetamido, (1–4C)alkanoyl, cyano, and trifluoromethyl.

Suitable substituents on AR2, AR2a, AR2b, AR3, AR3a, AR3b, AR4 and AR4a are (on an available nitrogen atom, where such substitution does not result in quaternization) (1–4C)alkyl, (1–4C)alkanoyl {wherein the (1–4C)alkyl and (1–4C)alkanoyl groups are optionally substituted by (preferably one) substituents independently selected from cyano, hydroxy, nitro, trifluoromethyl, (1–4C)alkyl S(O)$_q$— (q is 0, 1 or 2), (1–4C)alkoxy, (1–4C)alkoxycarbonyl, (1–4C)alkanoylamino, —CONRvRw or —NRvRw [wherein Rv is hydrogen or (1–4C)alkyl; Rw is hydrogen or (1–4C)alkyl]}, (2–4C)alkenyl, (2–4C)alkynyl, (1–4C)alkoxycarbonyl or oxo (to form an N-oxide).

Suitable pharmaceutically-acceptable salts include acid addition salts such as methanesulfonate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine N-ethylpiperidine, procaine, dibenzylamine, N, N-dibenzylethylamine, tris-(2-hydroxyethyl)amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the formula (I) may be administered in the form of a pro-drug which is broken down in the human or animal body to give a compound of the formula (I). A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the formula (I) or a pharmaceutically-acceptable salt thereof.

Various forms of prodrugs are known in the art, for examples see:
a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, Advanced Drug Delivery Reviews, 8, 1–38 (1992);
d) H. Bundgaard, et al., Journal of Pharmaceutical Sciences, 77, 285 (1988); and
e) N. Kakeya, et al., Chem Pharm Bull, 32, 692 (1984).

An in-vivo hydrolysable ester of a compound of the formula (I) or a pharmaceutically-acceptable salt thereof containing carboxy or hydroxy group is, for example, a pharmaceutically-acceptable ester which is hydrolysed in the human or animal body to produce the parent acid or alcohol.

Suitable pharmaceutically-acceptable esters for carboxy include (1–6C)alkoxymethyl esters for example methoxymethyl, (1–6C)alkanoyloxymethyl esters for example pivaloyloxymethyl, phthalidyl esters, (3–8C)cycloalkoxycarbonyloxy(1–6C)alkyl esters for example 1-cyclohexylcarbonyloxyethyl; 1,3-dioxolan-2-onylmethyl esters for example 5-methyl-1,3-dioxolan-2-ylmethyl; and (1–6C)alkoxycarbonyloxyethyl esters for example 1-methoxycarbonyloxyethyl and may be formed at any carboxy group in the compounds of this invention.

An in-vivo hydrolysable ester of a compound of the formula (I) or a pharmaceutically-acceptable salt thereof containing a hydroxy group or groups includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include (1–10C)alkanoyl, benzoyl, phenylacetyl and substituted benzoyl and phenylacetyl, (1–10C)alkoxycarbonyl (to give alkyl carbonate esters), di-(1–4C)alkylcarbamoyl and N-(di-(1–4C)alkylaminoethyl)-N-(1–4C)alkylcarbamoyl (to give carbamates), di-(1–4C)alkylaminoacetyl and carboxyacetyl. Examples of substituents on benzoyl and phenylacetyl include chloromethyl or aminomethyl, (1–4C)alkylaminomethyl and di-((1–4C)alkyl)aminomethyl, and morpholino or piperazino linked from a ring nitrogen atom via a methylene linking group to the 3- or 4-position of the benzoyl ring.

In addition a sulphoximine residue may be derivatised by a convenient biologically labile group to give a derivative suitable for use as a solubilising pro-drug.

Certain suitable in-vivo hydrolysable esters of a compound of the formula (I) are described within the definitions listed in this specification, for example esters described by the definition (Rc2d), and some groups within (Rc2c). Suitable in-vivo hydrolysable esters of a compound of the formula (I) are described as follows. For example, a 1,2-diol may be cyclised to form a cyclic ester of formula (PD1) or a pyrophosphate of formula (PD2):

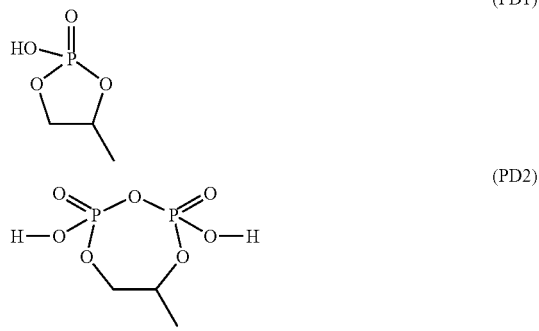

Particularly interesting are such cyclised pro-drugs when the 1,2-diol is on a (1–4C)alkyl chain linked to a carbonyl group in a substituent of formula Rc borne by a nitrogen atom in (TC4). Esters of compounds of formula (I) wherein the HO— function/s in (PD1) and (PD2) are protected by (1–4C)alkyl, phenyl or benzyl are useful intermediates for the preparation of such pro-drugs.

Further in-vivo hydrolysable esters include phosphoramidic esters, and also compounds of formula (I) in which any free hydroxy group, or sulfoxime group, independently forms a phosphoryl (npd is 1) or phosphiryl (npd is 0) ester of the formula (PD3) or (PS1), wherein npd is independently 0 or 1 for each oxo group:

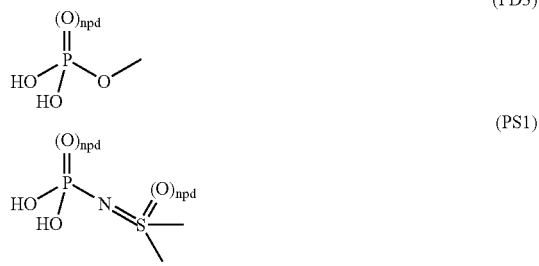

For the avoidance of doubt, phosphono is —P(O)(OH)$_2$; (1–4C)alkoxy(hydroxy)-phosphoryl is a mono-(1–4C) alkoxy derivative of —O—P(O)(OH)$_2$; and di-(1–4C) alkoxyphosphoryl is a di-(1–4C)alkoxy derivative of —O—P(O)(OH)$_2$.

Useful intermediates for the preparation of such esters include compounds containing a group/s of formula (PD3) in which either or both of the —OH groups in (PD3) is independently protected by (1–4C)alkyl (such compounds also being interesting compounds in their own right), phenyl or phenyl-(1–4C)alkyl (such phenyl groups being optionally substituted by 1 or 2 groups independently selected from (1–4C)alkyl, nitro, halo and (1–4C)alkoxy).

Thus, prodrugs containing groups such as (PD1), (PD2) and (PD3) may be prepared by reaction of a compound of formula (I) containing suitable hydroxy group/s with a suitably protected phosphorylating agent (for example, containing a chloro or dialkylamino leaving group), followed by oxidation (if necessary) and deprotection. Prodrugs containing a group such as (PS1) may be obtained by analagous chemistry.

When a compound of formula (I) contains a number of free hydroxy group, those groups not being converted into a prodrug functionality may be protected (for example, using a t-butyl-dimethylsilyl group), and later deprotected. Also, enzymatic methods may be used to selectively phosphorylate or dephosphorylate alcohol functionalities.

Other interesting in-vivo hydrolysable esters include, for example, those in which Rc is defined by, for example, $R^{14}C(O)O(1–6C)$alkyl-CO— (wherein $R^{14}$ is for example, benzyloxy-(1–4C)alkyl, or phenyl). Suitable substituents on a phenyl group in such esters include, for example, 4-(1–4C)piperazino-(1–4C)alkyl, piperazino-(1–4C)alkyl and morpholino-(1–4C)alkyl.

Where pharmaceutically-acceptable salts of an in-vivo hydrolysable ester may be formed this is achieved by conventional techniques. Thus, for example, compounds containing a group of formula (PD1), (PD2) and/or (PD3) may ionise (partially or fully) to form salts with an appropriate number of counter-ions. Thus, by way of example, if an in-vivo hydrolysable ester prodrug of a compound of formula (I) contains two (PD3) groups, there are four HO—P— functionalities present in the overall molecule, each of which may form an appropriate salt (i.e. the overall molecule may form, for example, a mono-, di-, tri- or tetra-sodium salt).

The compounds of the present invention have a chiral centre at the C-5 position of the isoxazoline ring. The pharmaceutically active enantiomer is of the formula (IA):

The present invention includes the pure enantiomer depicted above or mixtures of the 5R and 5S enantiomers, for example a racemic mixture. If a mixture of enantiomers is used, a larger amount (depending upon the ratio of the enantiomers) will be required to achieve the same effect as the same weight of the pharmaceutically active enantiomer. For the avoidance of doubt the enantiomer depicted above is the 5(R) isomer.

Furthermore, some compounds of the formula (I) may have other chiral centres, for example, certain sulfoxime compounds may be chiral at the sulfur atom. It is to be understood that the invention encompasses all such optical and diastereoisomers, and racemic mixtures, that possess antibacterial activity. It is well known in the art how to prepare optically-active forms (for example by resolution of the racemic form by recrystallisation techniques, by chiral synthesis, by enzymatic resolution, by biotransformation or by chromatographic separation) and how to determine antibacterial activity as described hereinafter.

Furthermore, some compounds of the formula (I), for example certain sulfoxime compounds may exist as cis- and trans-isomers. It is to be understood that the invention encompasses all such isomers, and mixtures thereof, that possess antibacterial activity.

The invention relates to all tautomeric forms of the compounds of the formula (I) that possess antibacterial activity.

It is also to be understood that certain compounds of the formula (I) can exist in solvated as well as unsolvated forms such as, for example, hydrated forms. It is to be understood that the invention encompasses all such solvated forms which possess antibacterial activity.

It is also to be understood that certain compounds of the formula (I) may exhibit polymorphism, and that the invention encompasses all such forms which possess antibacterial activity.

As stated before, we have discovered a range of compounds that have good activity against a broad range of Gram-positive pathogens including organisms known to be resistant to most commonly used antibiotics, together with activity against fastidious Gram negative pathogens such as *H. influenzae* & *M. catarrhalis*. They have good physical and/or pharmacokinetic properties in general, and favourable toxicological profiles.

Particularly preferred compounds of the invention comprise a compound of formula (I), or a pharmaceutically-acceptable salt or an in-vivo hydrolysable ester thereof, wherein the substituents Q, HET, T and other substituents mentioned above have values disclosed hereinbefore, or any of the following values (which may be used where appropriate with any of the definitions and embodiments disclosed hereinbefore or hereinafter):

In one embodiment of the invention are provided compounds of formula (I), or a pharmaceutically-acceptable salt or an in-vivo hydrolysable ester thereof, in which Q, HET, T and other substituents mentioned above have the values disclosed hereinbefore and Rs is selected from the group (Rsb).

In one embodiment is provided a compound of formula (I) as defined herein wherein Q is selected from Q1 to Q9. In another embodiment is provided a compound of formula (I) as defined herein wherein Q is Q10.

Preferably Q is selected from Q1, Q2, Q4, Q6 and Q9; especially Q1, Q2 and Q9; more particularly Q1 and Q2; and most preferably Q is Q1.

In one embodiment Rs has values (Rsa) to (Rsc1–3).
In another embodiment Rs has values (Rsd).
Preferable Rs groups are those of (Rsa) and (Rsb).
In one aspect, suitable values of (Rsa) are halo, amino and (2–4C)cycloalkenyl.
In another aspect a suitable value of (Rsd) is cyano.
In (Rsb) the substituted (1–4C)alkyl group is preferably a substituted methyl group.

In one aspect, suitable values for a substituent on a (1–4C)alkyl group in (Rsb) are cyano, azido, halo and (1–4C)alkyl-S(O)$_q$— wherein q=0, particularly wherein the (1–4C)alkyl group is a methyl group.

In (Rsb), when the (1–4C)alkyl group is substituted by a N-linked 5-membered heteroaryl ring it will be appreciated that the ring is aromatic and that when the ring is optionally substituted on an available carbon atom by oxo or thioxo then, when HET contains 1 to 3 further nitrogen heteroatoms, one of the further nitrogen heteroatoms is present as NH or as N-(1–4C)alkyl. Similarly, when the ring is optionally substituted on an available nitrogen atom by (1–4C) alkyl then the ring is substituted on an available carbon atom by oxo or thioxo. Preferred values for the N-linked 5-membered heteroaryl ring as a substituent in (Rsb) are the following rings (HET-P1 to HET-P5):—

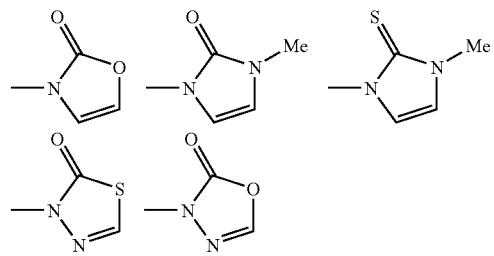

In (Rsc1) to (Rsc3), particular rings are morpholino, tetrahydropyridyl and dihydropyrrolyl.

Preferable (Rs) groups provided by optional F and/or Cl and/or Br and/or one cyano further substituents in (Rsa) and (Rsb) are, for example, Rs as trifluoromethyl, —CHF$_2$, —CH$_2$F, —CH$_2$Cl —CH$_2$Br, —CH$_2$CN, —CF$_2$NH(1–4C) alkyl, —CF$_2$CH$_2$OH, —CH$_2$OCF$_3$, —CH$_2$OCHF$_2$, —CH$_2$OCH$_2$F, —NHCF$_2$CH$_3$.

In another embodiment, T is selected from TAa1 and TAa2. In a further embodiment, T is TAa1.

Preferably T in Q10 is R$^1$(Rc)N— wherein R$^1$ is hydrogen, (1–4C)alkyl or hydroxy-(1–4C)alkyl), and Rc is as hereinbefore defined. Especially preferred for T in Q10 as R$^1$(Rc)N— is R$^1$ as hydrogen or methyl; and Rc as (Rc2), particularly wherein R$^{13}$ is (Rc2c).

In one embodiment T is selected from (TAa), (TAf), (TDb), (TC) or (TE); especially groups (TAa1 to TAa6), (TAf2), (TCb), (TCc), (TDb), and (TE); more particularly (TC2) to (TC13). In another embodiment T is selected from (TAa1 to TAa3), (TC5), (TC7), (TC9), (TC12), (TC13), (TE1) to (TE3); especially groups (TAa1 & 2), (TC5), (TC9), (TC12a & b), (TC13a) and (TE1a & b). In a further embodiment T is selected from TAa1, TAa2, TAf2 and TCc (for example morpholino). Especially preferred is each of the values of T in these embodiments when present in Q1 and Q2, particularly in Q1.

Preferable values for other substituents (which may be used where appropriate with any of the definitions and embodiments disclosed hereinbefore or hereinafter) are:—
(a) In one embodiment HET is a 6-membered heteroaryl as defined herein, and in another embodiment HET is a 5-membered heteroaryl as defined herein.
(b) When HET is a 5-membered heteroaryl as defined herein, preferably HET is 1,2,3-triazole (especially 1,2,3-triazol-1-yl), 1,2,4-triazole (especially 1,2,4-triazol-1-yl) and tetrazole (preferably tetrazol-2-yl).
(c) When HET is a 6-membered heteroaryl as defined herein, preferably HET is a di-hydro version of pyrimidine, pyridazine, pyrazine, 1,2,3-triazine, 1,2,4-triazine, 1,3,5-triazine and pyridine.
(d) In one aspect, preferably HET is unsubstituted. In another aspect HET is substituted as described in any embodiment or aspect described herein. Conveniently, when HET is a 5-membered heteroaryl as defined herein, it is substituted as described in any embodiment or aspect described herein. More conveniently, when HET is 1,2, 4-triazol-1-yl, it is substituted as described in any embodiment or aspect described herein.

(e) In one aspect preferably one of R² and R³ is hydrogen and the other fluoro. In another aspect both R² and R³ are fluoro.

(f) In (TC4) preferably >A₃-B₃- is >C═CH— or >N—CH₂—.

(g) Preferably Rc is R¹³CO— and preferably R¹³ is (1–4C)alkoxycarbonyl, hydroxy(1–4C)alkyl, (1–4C)alkyl (optionally substituted by one or two hydroxy groups, or by an (1–4C)alkanoyl group), (1–4C)alkylamino, dimethylamino(1–4C)alkyl, (1–4C)alkoxymethyl, (1–4C)alkanoylmethyl, (1–4C)alkanoyloxy(1–4C)alkyl, (1–5C)alkoxy or 2-cyanoethyl.

(h) More preferably R¹³ is 1,2-dihydroxyethyl, 1,3-dihydroxyprop-2-yl, 1,2,3-trihydroxyprop-1-yl, methoxycarbonyl, hydroxymethyl, methyl, methylamino, dimethylaminomethyl, methoxymethyl, acetoxymethyl, methoxy, methylthio, naphthyl, tert-butoxy or 2-cyanoethyl.

(i) Particularly preferred as R¹³ is 1,2-dihydroxyethyl, 1,3-dihydroxyprop-2-yl or 1,2,3-trihydroxyprop-1-yl.

(j) In another aspect preferably R¹³ is hydrogen, (1–10C)alkyl [optionally substituted by one or more hydroxy] or R¹⁴C(O)O(1–6C)alkyl.

For compounds of formula (I) preferred values for Rc are those in group (Rc2) when present in any of the definitions herein containing Rc—for example when present in compounds in which there is a (TC5) or (TC9) ring system.

In the definition of (Rc2c) the AR2a, AR2b, AR3a and AR3b versions of AR2 and AR3 containing groups are preferably excluded.

Especially preferred compounds of the present invention are of the formula (IB):

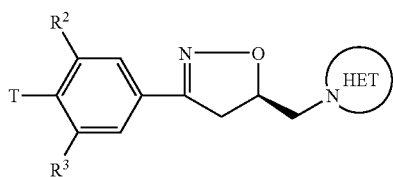

(IB)

wherein HET is 1,2,3-triazole (especially 1,2,3-triazol-1-yl), 1,2,4-triazole (especially 1,2,4-triazol-1-yl) and tetrazole (preferably tetrazol-2-yl) or HET is a di-hydro version of pyrimidine, pyridazine, pyrazine, 1,2,3-triazine, 1,2,4-triazine, 1,3,5-triazine and pyridine;

R² and R³ are independently hydrogen or fluoro; and

T is selected from (TAa1 to TAa6), (TAf1 to 6), (TC5), (TC7), (TC9), (TC12), (TC13) and (TE1) to (TE3); or in-vivo hydrolysable esters or pharmaceutically-acceptable salts thereof.

Further especially preferred compounds of the invention are of the formula (IB) wherein HET is 1,2,3-triazole (especially 1,2,3-triazol-1-yl), 1,2,4-triazole (especially 1,2,4-triazol-1-yl) or tetrazole (preferably tetrazol-2-yl);

R² and R³ are independently hydrogen or fluoro;

T is selected from (TAa1 & 2), (TC5), (TC9), (TC12a & b), (TC13a) and (TE1a & b); or in-vivo hydrolysable esters or pharmaceutically-acceptable salts thereof.

In the above aspects and preferred compounds of formula (IB), in (TAa1 to TAa6), preferably R⁵ʰ and R⁶ʰ are hydrogen and R⁴ʰ is selected from cyano, (1–4C)alkoxycarbonyl, —CONRcRv (preferably with Rc as hydrogen or (1–4C) alkyl), hydroxy-(1–4C)alkyl and —NRcRv(1–4C)alkyl; wherein Rv is hydrogen or (1–4C)alkyl and Rc is as defined in (Rc2) and especially R¹³CO— wherein R¹³ is preferably (1–4C)alkoxycarbonyl, hydroxy(1–4C)alkyl, (1–4C)alkyl (optionally substituted by one or two hydroxy groups, or by an (1–4C)alkanoyl group), (1–4C)alkylamino, dimethylamino(1–4C)alkyl, (1–4C)alkoxymethyl, (1–4C)alkanoylmethyl, (1–4C)alkanoyloxy(1–4C)alkyl, (1–5C)alkoxy or 2-cyanoethyl.

In the above aspects and preferred compounds of formula (IB), in (TC5), (TC7), (TC9), preferably Rc is as defined in (Rc2) and especially R¹³CO— wherein R¹³ is preferably (1–4C)alkoxycarbonyl, hydroxy(1–4C)alkyl, (1–4C)alkyl (optionally substituted by one or two hydroxy groups, or by an (1–4C)alkanoyl group), (1–4C)alkylamino, dimethylamino(1–4C)alkyl, (1–4C)alkoxymethyl, (1–4C)alkanoylmethyl, (1–4C)alkanoyloxy(1–4C)alkyl, (1–5C)alkoxy or 2-cyanoethyl.

In the above aspects and preferred compounds of formula (IB), in (TC12), (TC13) and (TE1) to (TE3); and especially in (TC12a & b), (TC13a) and (TE1a & b); preferably X₁ₘ is O═ and X₂ₘ is R₂ₛ—(E)ₘₛ—N—, and vice versa; and when ms is 0, R₂ is preferably selected from (i) hydrogen, a (1–6C)alkyl group {optionally monosubstituted by (1–4C)alkanoyl group, cyano, cyano-imino, (1–4C)alkoxy, trifluoromethyl, (1–4C)alkoxycarbonyl, phenyl (optionally substituted as for AR1 defined herein), optionally substituted heteroaryl group of the formula AR2, AR2a, AR2b, AR3, AR3a, AR3b, AR4, AR4a or CY1 all as defined (and optionally substituted as defined) herein, (1–4C)alkylS(O)q— (q is 0, 1 or 2); or optionally substituted by one or more fluoro groups (including geminal disubstitution); or optionally substituted by one or more hydroxy groups (excluding geminal disubstitution), and/or optionally further substituted, by no more than one of each of, oxo, —NRvRw [wherein Rv is hydrogen or (1–4C)alkyl; Rw is hydrogen or (1–4C) alkyl], (1–6C)alkanoylamino, (1–4C)alkoxycarbonylamino, N—(1–4C)alkyl-N—(1–6C)alkanoylamino, (1–4C)alkylS(O)ₚNH— or (1–4C)alkylS(O)ₚ—((1–4C)alkyl)N— (p is 1 or 2)}; or (ii) an optionally substituted aryl or optionally substituted heteroaryl group of the formula AR1, AR2, AR2a, AR2b, AR3, AR3a, AR3b, AR4, AR4a or CY1 all as defined (and optionally substituted as defined) herein; or (where ms is 0 only), (iii) cyano, —CO—NRvRw, —CO—NRvRw', —SO₂—NRvRw, —SO₂—NRvRw' [wherein Rv is hydrogen or (1–4C)alkyl; Rw is hydrogen or (1–4C)alkyl; Rw' is phenyl (optionally substituted as for AR1 defined herein), or a heteroaryl group selected from AR2, AR2a, AR2b, AR3, AR3a, AR3b, AR4, AR4a (optionally substituted as defined herein)], (1–4C)alkoxycarbonyl, trifluoromethyl; and when ms is 1, E is preferably —CO— or —SO₂— and R₂, is preferably selected from:

(i) (1–6C)alkyl {optionally monosubstituted by cyano, cyano-imino, (1–4C)alkoxy, trifluoromethyl, (1–4C) alkoxycarbonyl, phenyl (optionally substituted as for AR1 defined herein), optionally substituted heteroaryl group of the formula AR2, AR2a, AR2b, AR3, AR3a, AR3b, AR4, AR4a or CY1 all as defined (and optionally substituted as defined) herein, (1–4C)alkylS(O)q— (q is 0, 1 or 2); and/or (with the proviso that where R₂ₛ is —SO₂— or —O—CO— not on the first carbon atom of the (1–6C) alkyl chain) optionally substituted by one or more groups (including geminal disubstitution) each independently selected from hydroxy and fluoro, and/or optionally monosubstituted by —NRvRw [wherein Rv is hydrogen or (1–4C)alkyl; Rw is hydrogen or (1–4C)alkyl], (1–6C)alkanoylamino, (1–4C)alkoxycarbonylamino, N—(1–4C)alkyl-N—(1–6C)alkanoylamino, (1–4C)alkylS(O)$_p$NH— or (1–4C)alkylS(O)$_p$—((1–4C)alkyl)N— (p is 1 or 2)}; or (ii) an optionally substituted aryl or heteroaryl group of the formula AR1, AR2, AR2a, AR2b, AR3, AR3a, AR3b, AR4, AR4a or CY1 all as defined (and optionally substituted as defined) herein.

In the above aspects and preferred compounds of formula (IB), preferable optional substituents Rs on HET are fluoromethyl, difluoromethyl, trifluoromethyl, chloromethyl, bromomethyl, cyanomethyl, cyano, amino, azido, alkylthioalkyl such as methylthiomethyl, or 2-propynyl.

In all of the above aspects and preferred compounds of formula (IB), in-vivo hydrolysable esters are preferred where appropriate, especially phosphoryl esters (as defined by formula (PD3) with npd as 1).

In all of the above definitions the preferred compounds are as shown in formula (IA), i.e. the pharmaceutically active (5(R)) enantiomer.

Particular compounds of the present invention include the following Examples, in particular Example Nos. 4 and 7, and the individual (5R) isomers thereof.

Process Section:

In a further aspect the present invention provides a process for preparing a compound of formula (I), or a pharmaceutically-acceptable salt or an in-vivo hydrolysable ester thereof.

It will be appreciated that during certain of the following processes certain substituents may require protection to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons).

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art.

A compound of the formula (I), or a pharmaceutically-acceptable salt or an in-vivo hydrolysable ester thereof, may be prepared by any process known to be applicable to the preparation of chemically-related compounds. Such processes, when used to prepare a compound of the formula (I), or a pharmaceutically-acceptable salt or an in-vivo hydrolysable ester thereof, are provided as a further feature of the invention and are illustrated by the following representative Examples.

Necessary starting materials may be obtained by standard procedures of organic chemistry (see, for example, Advanced Organic Chemistry (Wiley-Interscience), Jerry March). The preparation of such starting materials is described within the accompanying non-limiting Examples (in which, for example, 3,5-difluorophenyl, 3-fluorophenyl and (des-fluoro)phenyl containing intermediates may all be prepared by analagous procedures; or by alternative procedures—for example, the preparation of (T group)-(fluoro)phenyl intermediates by reaction of a (fluoro)phenylstannane with, for example, a pyran or (tetrahydro)pyridine compound, may also be prepared by suitable anion chemistry. Such chemistry is illustrated, for example, in WO97/30995 for the preparation of oxazolidinone compounds, but analogous procedures to those illustrated may be applied for the preparation of the isoxazoline compounds, and necessary starting materials, described herein, which chemistry is within the ordinary skill of an organic chemist.

Information on the preparation of necessary starting materials or related compounds (which may be adapted to form necessary starting materials) may also be found, for example, in the following patent and Application Publications, the contents of the relevant process sections of which are hereby incorporated herein by reference: WO 98/07708, WO 99/41244; WO 99/43671; WO 01/40222 and WO 01/46185.

The skilled organic chemist will be able to use and adapt the information contained and referenced within the above references to obtain necessary starting materials.

Thus, the present invention also provides that the compounds of the formula (I), and pharmaceutically-acceptable salts and in-vivo hydrolysable esters thereof, can be prepared by a process (a) to (h) as follows (wherein the variables are as defined above unless otherwise stated) and illustrated in the Schemes and notes below:

(a) by modifying a substituent in or introducing a substituent into another compound of formula (I). Such changes may be usefully made in many positions of compounds of formula (I), for instance a heterocyclyl group linked through nitrogen (optionally substituted on a carbon other than a carbon atom adjacent to the linking nitrogen ring atom) may be converted into another heterocyclyl group linked through nitrogen (optionally substituted on a carbon other than a carbon atom adjacent to the linking nitrogen ring atom) by introduction of a new ring substituent or by refunctionalisation of an existing ring substituent, for instance by modifying the 4-substituent of a 4-substituted 1,2,3-triazol-1-yl group; or for instance such changes may be usefully made in the group Q; for example an alkylthio group may be oxidised to an alkylsulfinyl or alkysulfonyl group, for instance a group TC4 wherein G is the sulfur atom of e.g. thiomorpholine may be oxidized to a thiomorpholine S-oxide or S,S-dioxide, or to a thiomorpholine sulfimine or stepwise to a sulfoximine; and it is also possible to convert one Rc group into another Rc group as a final step in the preparation of a compound of the formula (I), for example, acylation of a group of formula (TC5) wherein Rc is hydrogen;

(b) by reaction of a compound of formula (II):

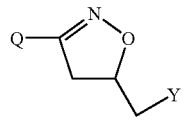

(II)

wherein Y is a displaceable group (which may be (i) generated in-situ, for example under Mitsunobu conditions, or (ii) preformed, such as chloro or mesylate) with a compound of the formula (III):

HET (III)

wherein HET is HET-H free-base form or HET–anion formed from the free base form;

or (c) by reaction of a compound of formula (IV):

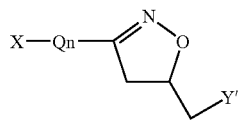

(IV)

wherein Y' is HET, X is a displaceable substituent (such as fluoro) and Qn is as defined herein for Q1–Q8 but with X in place of the substituent T; with a compound of the formula (V):

T (V)

wherein T is T-H free-base form or T–anion formed from the free base form T-H as hereinabove defined for T; or (d) by reaction of a compound of the formula (VI):

$Q-C\equiv N^+-O^-$ (VI)

wherein the group $C\equiv N^+-O^-$ is a nitrile oxide; with an allylic derivative such as an olefin of the formula (VII):

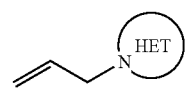

(VII)

(e) by transition metal medicated coupling of a compound of formula (IV), wherein Y' is HET, X is a replaceable substituent (such as trimethylstannyl) and Qn is as defined herein for Q1–Q8 but with X in place of the substituent T; with a compound of the formula (VIII):

T-X' (VIII)

wherein X and X' are complementary substitutents capable of entering into such coupling reactions; or (f) for HET as optionally substituted 1,2,3-triazole compounds of formula (I) may be made by cycloaddition via the azide (wherein e.g. Y in (II) is azide) to acetylenes, or to acetylene equivalents such as optionally substituted cylcohexa-1,4-dienes or optionally substituted ethylenes bearing eliminatable substituents such as arylsulfonyl; or (g) for HET as 4-substituted 1,2,3-triazole compounds of formula (I) may be made by reacting aminomethylisoxazolines with 1,1-dihaloketone sulfonylhydrazones;

(h) for HET as 4-substituted 1,2,3-triazole compounds of formula (I) may also be made by reacting azidomethyl isoxazolines with terminal alkynes using Cu(1) catalysis;

and thereafter if necessary: (i) removing any protecting groups; (ii) forming a pharmaceutically-acceptable salt; (iii) forming an in-vivo hydrolysable ester.

Deprotection, salt formation or in-vivo hydrolysable ester formation may each be provided as a specific final process step.

The N-linked hetereocycle (HET) can of course be prepared early in the overall synthesis, and then other functional groups changed.

General guidance on reaction conditions and reagents may be obtained in Advanced Organic Chemistry, 4$^{th}$ Edition, Jerry March (publisher: J. Wiley & Sons), 1992. Necessary starting materials may be obtained by standard procedures of organic chemistry, such as described in this process section, in the Examples section or by analogous procedures within the ordinary skill of an organic chemist. Certain references are also provided which describe the preparation of certain suitable starting materials, the contents of which are incorporated here by reference. Processes analogous to those described in the references may also be used by the ordinary organic chemist to obtain necessary starting materials.

(a) Methods for converting substituents into other substituents are known in the art. by using standard chemistry (see for example, Comprehensive Organic Functional Group Transformations (Pergamon), Katritzky, Meth-Cohn & Rees); for example: a hydroxy group may be converted into a silyloxy group; an azido or an acylamino or thioacylamino group, for instance an acetamide group (optionally substituted or protected on the amido-nitrogen atom); into an acyloxy group, for instance an acetoxy group; a heterocyclylamino group (optionally substituted or protected on the amino-nitrogen atom), for instance an isoxazol-3-ylamino group or a 1,2,5-thiadiazol-3-ylamino group; a heterocyclyl group linked through nitrogen (optionally substituted on a carbon other than a carbon atom adjacent to the linking nitrogen ring atom), for instance an optionally substituted 1,2,3-triazol-1-yl group; or an amidino group, for instance an 1-(N-cyanoimino)ethylamino group; a hydroxy group may be alkylated to a methoxy group, a hydroxy group may be converted into a halomethyl group, or into a cyanomethyl group; or into an alkylthio-, an arylthio- or a heteroarylthio- group (see, for example, Tet. Lett., 585, 1972); such conversions of the hydroxy group taking place directly (for instance by acylation or Mitsunobu reaction) or through the intermediacy of one or more derivatives (for instance a mesylate or an azide); moreover, a hydroxy-group may be oxidized to a carbonyl group including a carboxylic acid group.

an acyloxy group may be converted into a hydroxy group or into the groups that may be obtained from a hydroxy group (either directly or through the intermediacy of a hydroxy group);

a silyloxy group may be converted into a hydroxy group or into the groups that may be obtained from a hydroxy group (either directly or through the intermediacy of a hydroxy group);

an acylamino group or thioacylamino group may be converted into another acylamino group or thioacylamino group; into a heterocyclylamino group (optionally substituted or protected on the amino-nitrogen atom);

a carbonyl group can be reduced to a hydroxy group and a carboxylic acid group or a derivative thereof can be reduced to a carbonyl group or to a hydroxy group;

an alkylthio group may be oxidised to an alkylsulfinyl or alkysulfonyl group;

a cyano group may be reduced to an amino group, a nitro group may be reduced to an amino group; a carbonyl group may be converted into a thiocarbonyl group (eg. using Lawsson's reagent) or a bromo group converted to an alkylthio group. It is possible in this way to interconvert compounds of formula (I).

(b)(i) Reaction (b)(i) is performed under Mitsunobu conditions, for example, in the presence of tri-n-butylphosphine and diethyl azodicarboxylate (DEAD) in an organic solvent such as THF, and in the temperature range 0° C.–60° C., but preferably at ambient temperature. Details of Mitsunobu reactions are contained in Tet. Letts., 31, 699, (1990); The Mitsunobu Reaction, D. L. Hughes, Organic Reactions, 1992, Vol. 42, 335–656 and Progress in the Mitsunobu Reaction, D. L. Hughes, Organic Preparations and Procedures International, 1996, Vol. 28, 127–164.

(b)(ii) Reactions (b)(ii) are performed conveniently in the presence of a suitable base such as, for example, an alkali or alkaline earth metal carbonate, alkoxide or hydroxide, for example sodium carbonate or potassium carbonate, or, for example, an organic amine base such as, for example, pyridine, 2,6-lutidine, collidine, 4-dimethylaminopyridine, triethylamine, morpholine or diazabicyclo-[5.4.0]undec-7-ene, the reaction is also preferably carried out in a suitable inert solvent or diluent, for example methylene chloride, acetonitrile, tetrahydrofuran, 1,2-dimethoxyethane, N,N-dimethylformamide, N. N-dimethylacetamide, N-methylpyrrolidin-2-one or dimethylsulfoxide at and at a temperature in the range 25–60° C.

Where Y is a displaceable group, suitable values for Y are for example, a halogeno or sulfonyloxy group, for example a chloro, bromo, methanesulfonyloxy or toluene-4-sulfonyloxy group. When Y is chloro, the compound of the formula (II) may be formed by reacting a compound of the formula (II) wherein Y is hydroxy (hydroxy compound) with a chlorinating agent. For example, by reacting the hydroxy compound with thionyl chloride, in a temperature range of ambient temperature to reflux, optionally in a chlorinated solvent such as dichloromethane or by reacting the hydroxy compound with carbon tetrachloride/triphenyl phosphine in dichloromethane, in a temperature range of 0° C. to ambient temperature. A compound of the formula (II) wherein Y is chloro or iodo may also be prepared from a compound of the formula (II) wherein Y is mesylate or tosylate, by reacting the latter compound with lithium chloride or lithium iodide and crown ether, in a suitable organic solvent such as THF, in a temperature range of ambient temperature to reflux.

When Y is (1–4C)alkanesulfonyloxy or tosylate the compound (II) may be prepared by reacting the hydroxy compound with (1–4C)alkanesulfonyl chloride or tosyl chloride in the presence of a mild base such as triethylamine or pyridine.

When Y is a phosphoryl ester (such as $PhO_2$—P(O)—O—) or $Ph_2$—P(O)—O— the compound (II) may be prepared from the hydroxy compound under standard conditions.

(c) Compounds of the formula (I) may be obtained by nucleophilic displacement of a leaving group X from a suitably substituted derivative (IV). Suitable values for X include fluoro, chloro, or mesyloxy. Suitable nucleophiles include saturated or fully or partially unsaturated nitrogen heterocycles containing an ionisable NH group.

The starting materials of formula (II) may be obtained from compounds wherein Y as HET is obtained via a compound in which Y is hydroxy or Y is a group that may be converted into a HET ring.

If not commercially available, the optionally substituted nitrogen heterocycles used in this method (c) may be prepared by procedures which are selected from standard chemical techniques, techniques which are analogous to the synthesis of known, structurally similar compounds, or techniques which are analogous to the procedures described in the Examples. For example, standard chemical techniques are as described in Houben Weyl, Methoden der Organische Chemie.

This method is illustrated in Scheme 2 and in the accompanying non-limiting Examples.

The chemistry of process (c) may also be utilised to prepare compounds of formula (II) wherein Y is hydroxy or a group that may be converted into a HET ring, and then process (b) or other suitable chemistry used to prepare compounds of formula (I).

(d) Compounds of the formula (I) may be obtained as described in the references cited herein, or obtained by adapting the chemistry described therein. Scheme 2 also shows an example of the preparation of the isoxazoline ring via the nitrile oxide (prepared from the relevant oxime).

If not commercially available, the compounds of formula (VII) and the substituted oximes or nitromethanes used as precursors of the nitrile oxides of the formula (VI) may be prepared by procedures which are selected from standard chemical techniques, techniques which are analogous to the synthesis of known, structurally similar compounds, or techniques which are analogous to the procedures described in the Examples. For example, standard chemical techniques are as described in Houben Weyl, Methoden der Organische Chemie.

The chemistry of process (d) may also be utilised to prepare compounds of formula (II) wherein Y is hydroxy (for example using an allyl alcohol in place of the compound of formula (VII)) or a group that may be converted into a HET ring, and then process (b) or other suitable chemistry used to prepare compounds of formula (I).

(e) Compounds of formula (I) may be obtained by coupling together two appropriately substituted fragments to form a carbon-carbon bond in the place of two substitutents X and X'. X and X' may be selected from substituents such as chloro, bromo, iodo, trifluoromethanesulfonyloxy, trialkylstannyl, or a boronic acid residue provided that the selected substituents X and X' form a pair of complementary substituents known in the art to be suitable pairs of substituents for transition metal mediated coupling reactions. For instance one of X and X' may be trimethyl stannyl and the other may be triflate, as shown in the Scheme 3.

If not commercially available, the X and X' substituted fragments used as coupling partners in the transition metal mediated coupling reaction may be prepared by procedures which are selected from standard chemical techniques, techniques which are analogous to the synthesis of known, structurally similar compounds, or techniques which are analogous to the procedures described in the Examples. For example, standard chemical techniques are as described in Houben Weyl, Methoden der Organische Chemie.

The chemistry of process (e) may also be utilised to prepare compounds of formula (II) wherein Y is hydroxy or a group that may be converted into a HET ring, and then process (b) or other suitable chemistry used to prepare compounds of formula (I).

(f) The cycloaddition reaction to form 1,2,3 triazoles from the corresponding azide is performed under conventional conditions. The reaction may use acetylenes or equivalent synthons that react as olefins and then eliminate the elements of a molecule to regenerate a double bond between the carbon atoms of the original olefin. Suitable olefins or their close analogues include those able to eliminate cyclopentadiene, optionally substituted naphthalenes, secondary amines, or sulfinic or sulfenic acids have been described in the litereature as synthons for alkynes.

(g) 4-Substituted 1,2,3-triazoles may be constructed from a primary amino compound acoording to the method of Sakai et al. by reacting it with sulfonylhydrazones of 1,1-dihalomethylketones. (see for example Sakai et al., *Bull. Chem. Soc. Japan,* 1985, 59, 179); as illustrated in Scheme Ic;

(h) 4-Substituted 1,2,3-triazoles may be constructed from terminal alkynes in a mild and regioselective reaction according to the method of Sharpless. (see V. V. Rostov, L. G. Green, V. V. Folkin, and K. B. Sharpless, *Angew. Chem. Int. Ed.,* 2002, 41, 2596); ); as illustrated in Scheme Ib; The preparation of suitable alkynes or their close analogues from simpler commercially available acetylenes such as acetylene itself or trimethylsilylacetylene is well-known in the chemical literature;

Compounds of the formula (II) wherein Y is azide may be obtained using standard procedure, for example from the corresponding compounds in which Y is hydroxy or mesylate.

Certain novel intermediates utilised in the above processes are provided as a further feature of the invention.

The following Schemes illustrate process chemistry which allows preparation of compounds of the formula (I). The Schemes may be genericised by the skilled man to apply to compounds within the present specification which are not specifically illustrated in the Schemes (for example to HET as a 6-membered ring as defined herein).

Scheme 1

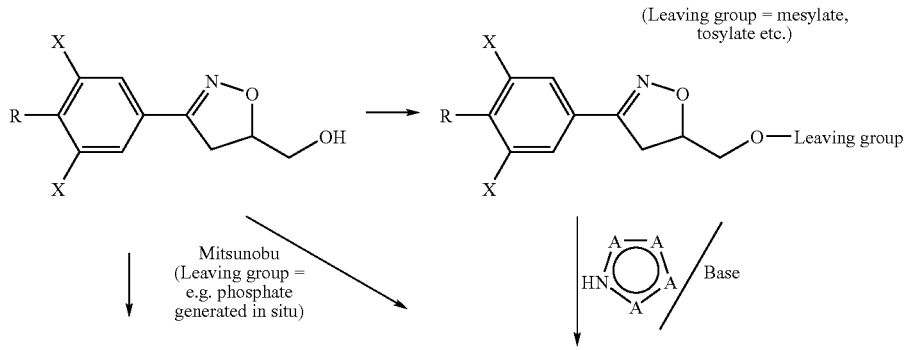

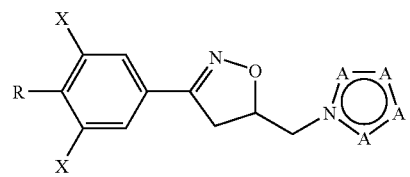

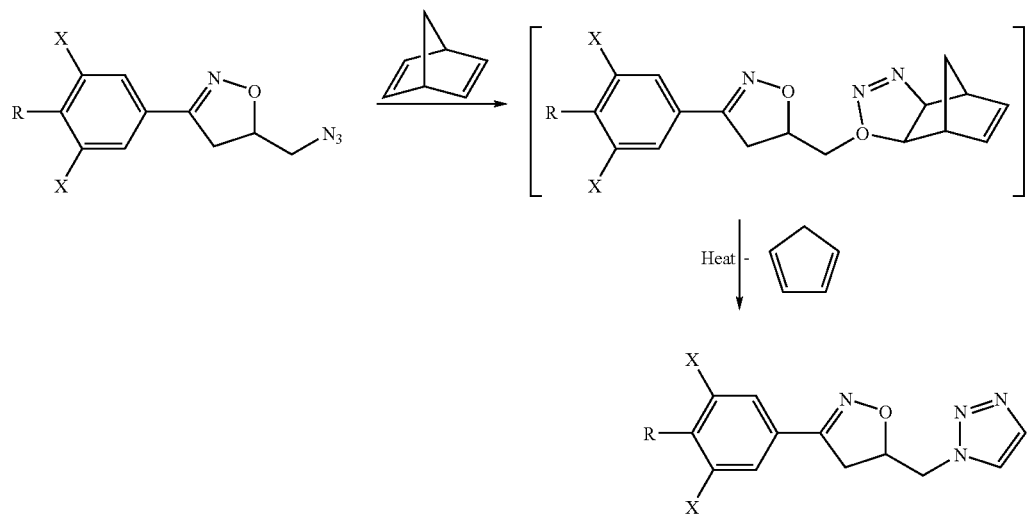
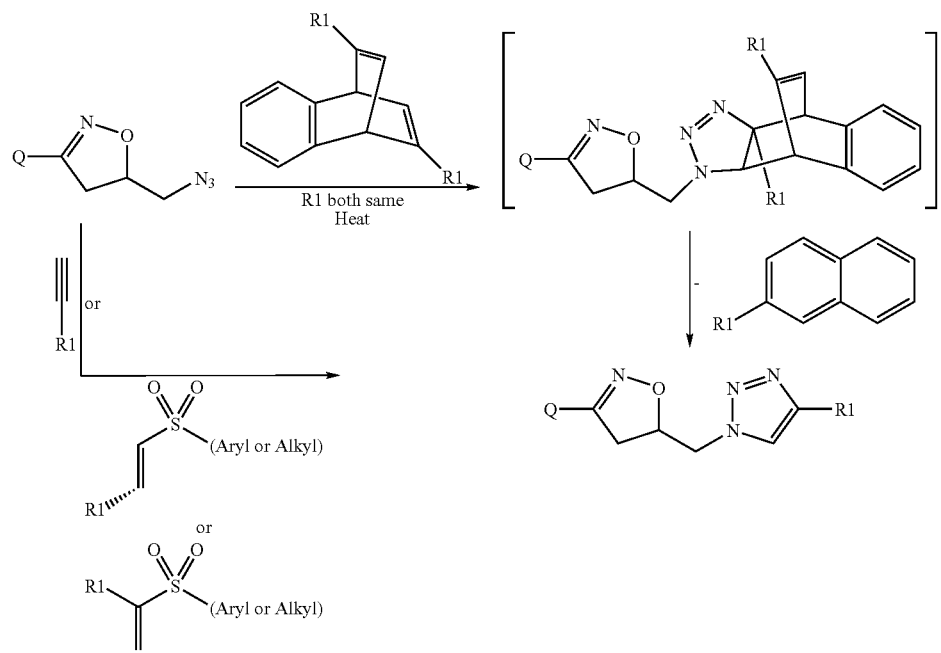
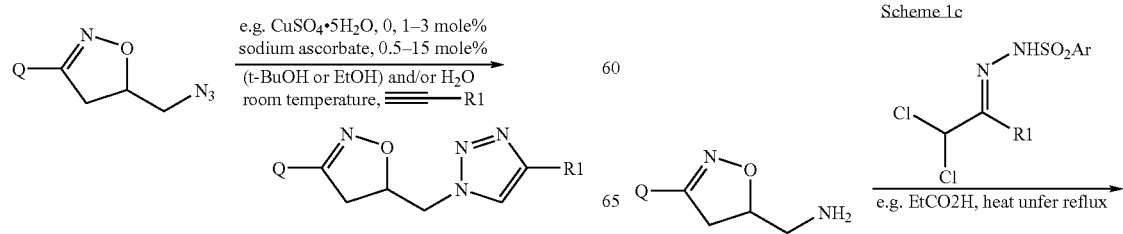

-continued

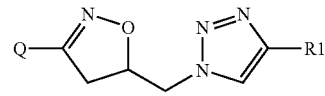

Scheme 1d

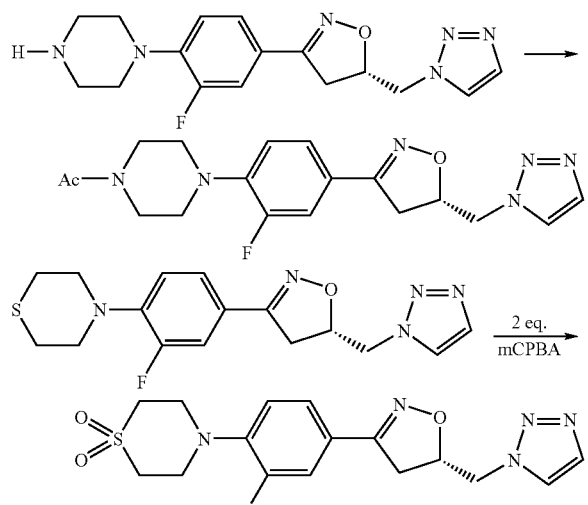

Scheme 3

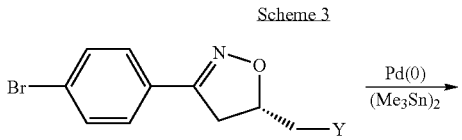

Prepared as in the general
route given in (d).
Y may be an N-linked
5-membered heterocycle
or a precursor thereof

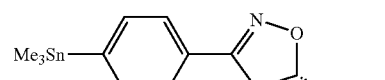

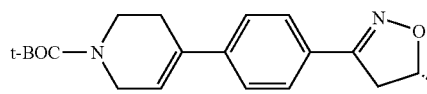

Other carbon linked species can be made analogously

The removal of any protecting groups, the formation of a pharmaceutically-acceptable salt and/or the formation of an in-vivo hydrolysable ester are within the skill of an ordinary Scheme 2

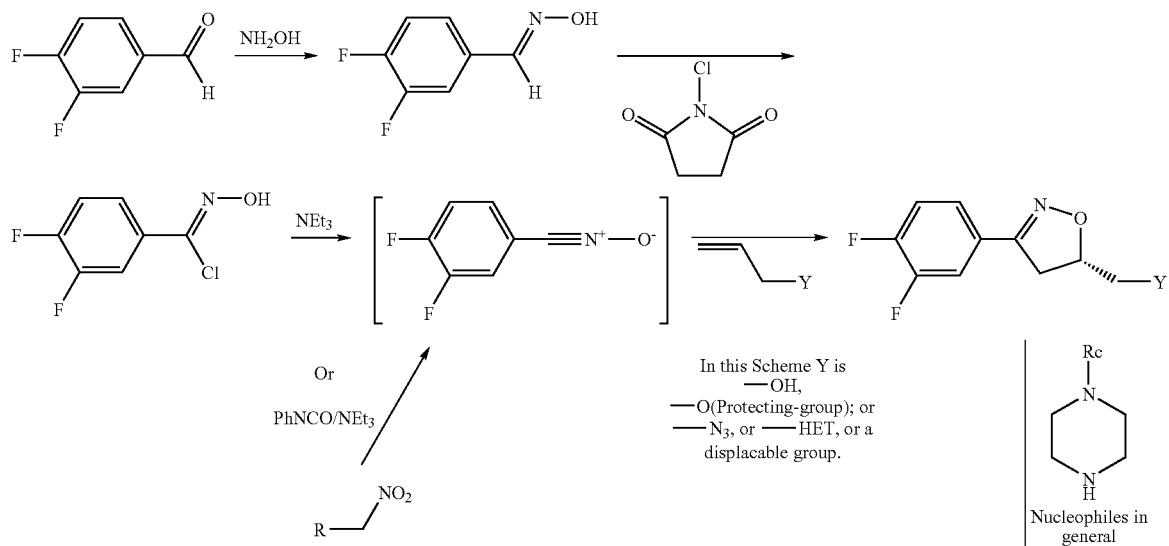

In this Scheme Y is
—OH,
—O(Protecting-group); or
—N$_3$, or —HET, or a
displaceable group.

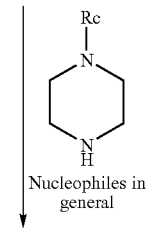

Nucleophiles in
general

Other activating agents/base
pairs may be used:
BOC$_2$O; TMS—Cl; EtOOCCl/DMAP

R is Q or a precursor to Q

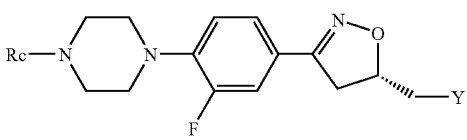

organic chemist using standard techniques. Furthermore, details on the these steps, for example the preparation of in-vivo hydrolysable ester prodrugs has been provided in the section above on such esters, and in certain of the following non-limiting Examples.

When an optically active form of a compound of the formula (I) is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the formula (I) is required, it may be obtained by carrying out one of the above procedures using a pure regioisomer as a starting material, or by resolution of a mixture of the regioisomers or intermediates using a standard procedure.

According to a further feature of the invention there is provided a compound of the formula (I), or a pharmaceutically-acceptable salt, or in-vivo hydrolysable ester thereof for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt, or in-vivo hydrolysable ester thereof.

The invention also provides a compound of the formula (I), or a pharmaceutically-acceptable salt, or in-vivo hydrolysable ester thereof, for use as a medicament; and the use of a compound of the formula (I) of the present invention, or a pharmaceutically-acceptable salt, or in-vivo hydrolysable ester thereof, in the manufacture of a medicament for use in the production of an antibacterial effect in a warm blooded animal, such as man.

In order to use a compound of the formula (I), an in-vivo hydrolysable ester or a pharmaceutically-acceptable salt thereof, including a pharmaceutically-acceptable salt of an in-vivo hydrolysable ester, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I), an in-vivo hydrolysable ester or a pharmaceutically-acceptable salt thereof, including a pharmaceutically-acceptable salt of an in-vivo hydrolysable ester, and a pharmaceutically-acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, aerosols (or sprays), drops and sterile injectable aqueous or oily solutions or suspensions.

In addition to the compounds of the present invention the pharmaceutical composition of this invention may also contain or be co-administered (simultaneously, sequentially or separately) with one or more known drugs selected from other clinically useful antibacterial agents (for example, β-lactams or aminoglycosides) and/or other anti-infective agents (for example, an antifungal triazole or amphotericin). These may include carbapenems, for example meropenem or imipenem, to broaden the therapeutic effectiveness. Compounds of this invention may also contain or be co-administered with bactericidal/permeability-increasing protein (BPI) products or efflux pump inhibitors to improve activity against gram negative bacteria and bacteria resistant to antimicrobial agents.

A suitable pharmaceutical composition of this invention is one suitable for oral administration in unit dosage form, for example a tablet or capsule which contains between 1 mg and 1 g of a compound of this invention, preferably between 100 mg and 1 g of a compound. Especially preferred is a tablet or capsule which contains between 50 mg and 800 mg of a compound of this invention, particularly in the range 100 mg to 500 mg.

In another aspect a pharmaceutical composition of the invention is one suitable for intravenous, subcutaneous or intramuscular injection, for example an injection which contains between 0.1% w/v and 50% w/v (between 1 mg/ml and 500 mg/ml) of a compound of this invention.

Each patient may receive, for example, a daily intravenous, subcutaneous or intramuscular dose of 0.5 mgkg$^{-1}$ to 20 mgkg$^{-1}$ of a compound of this invention, the composition being administered 1 to 4 times per day. In another embodiment a daily dose of 5 mgkg$^{-1}$ to 20 mgkg$^{-1}$ of a compound of this invention is administered. The intravenous, subcutaneous and intramuscular dose may be given by means of a bolus injection. Alternatively the intravenous dose may be given by continuous infusion over a period of time. Alternatively each patient may receive a daily oral dose which may be approximately equivalent to the daily parenteral dose, the composition being administered 1 to 4 times per day.

A pharmaceutical composition to be dosed intravenously may contain advantageously (for example to enhance stability) a suitable bactericide, antioxidant or reducing agent, or a suitable sequestering agent.

In the above other, pharmaceutical composition, process, method, use and medicament manufacture features, the alternative and preferred embodiments of the compounds of the invention described herein also apply.

Antibacterial Activity:

The pharmaceutically-acceptable compounds of the present invention are useful antibacterial agents having a good spectrum of activity in-vitro against standard Gram-positive organisms, which are used to screen for activity against pathogenic bacteria. Notably, the pharmaceutically-acceptable compounds of the present invention show activity against enterococci, pneumococci and methicillin resistant strains of *S. aureus* and coagulase negative staphylococci, together with *haemophilus* and *moraxella* strains. The antibacterial spectrum and potency of a particular compound may be determined in a standard test system.

The (antibacterial) properties of the compounds of the invention may also be demonstrated and assessed in-vivo in conventional tests, for example by oral and/or intravenous dosing of a compound to a warm-blooded mammal using standard techniques.

The following results were obtained on a standard in-vitro test system. The activity is described in terms of the minimum inhibitory concentration (MIC) determined by the agar-dilution technique with an inoculum size of $10^4$ CFU/spot. Typically, compounds are active in the range 0.01 to 256 μg/ml.

Staphylococci were tested on agar, using an inoculum of $10^4$ CFU/spot and an incubation temperature of 37° C. for 24 hours—standard test conditions for the expression of methicillin resistance.

Streptococci and enterococci were tested on agar supplemented with 5% defibrinated horse blood, an inoculum of $10^4$ CFU/spot and an incubation temperature of 37° C. in an atmosphere of 5% carbon dioxide for 48 hours—blood is required for the growth of some of the test organisms. Fastidious Gram negative organisms were tested in Mueller-Hinton broth, supplemented with hemin and NAD, grown aerobically for 24 hours at 37° C., and with an innoculum of $5 \times 10^4$ CFU/well.

For example, the following results were obtained for the compound of Example 7:

| Organism | | MIC (μg/ml) |
| --- | --- | --- |
| *Staphylococcus aureus*: | MSQS | 8 |
| | MRQR | 16 |
| *Streptococcus pneumoniae* | | 1 |
| *Streptococcus pyogenes* | | 2 |
| *Haemophilus influenzae* | | 32 |
| *Moraxella catarrhalis* | | 32 |

MSQS = methicillin sensitive and quinolone sensitive
MRQR = methicillin resistant and quinolone resistant Certain intermediates and/or Reference Examples described hereinafter within the scope of the invention may also possess useful activity, and are provided as a further feature of the invention.

The invention is now illustrated but not limited by the following Examples in which unless otherwise stated:—

(i) evaporations were carried out by rotary evaporation U and work-up procedures were carried out after removal of residual solids by filtration;

(ii) operations were carried out at ambient temperature, that is typically in the range 18–26° C. and without exclusion of air unless otherwise stated, or unless the skilled person would otherwise work under an inert atmosphere;

(iii) column chromatography (by the flash procedure) was used to purify compounds and was performed on Merck Kieselgel silica (Art. 9385) unless otherwise stated;

(iv) yields are given for illustration only and are not necessarily the maximum attainable;

(v) the structure of the end-products of the invention were generally confirmed by NMR and mass spectral techniques [proton magnetic resonance spectra were generally determined in DMSO-$d_6$ unless otherwise stated using a Varian Gemini 2000 spectrometer operating at a field strength of 300 MHz, or a Bruker AM250 spectrometer operating at a field strength of 250 MHz; chemical shifts are reported in parts per million downfield from tetramethysilane as an internal standard (δ scale) and peak multiplicities are shown thus: s, singlet; d, doublet; AB or dd, doublet of doublets; dt, doublet of triplets; dm, doublet of multiplets; t, triplet, m, multiplet; br, broad; fast-atom bombardment (FAB) mass spectral data were generally obtained using a Platform spectrometer (supplied by Micromass) run in electrospray and, where appropriate, either positive ion data or negative ion data were collected];

(vi) each intermediate was purified to the standard required for the subsequent stage and was characterised in sufficient detail to confirm that the assigned structure was correct; purity was assessed by HPLC, TLC, or NMR and identity was determined by infra-red spectroscopy (IR), mass spectroscopy or NMR spectroscopy as appropriate;

(vii) in which the following abbreviations may be used:—

DMF is N,N-dimethylformamide; DMA is N,N-dimethylacetamide; TLC is thin layer chromatography; HPLC is high pressure liquid chromatography; MPLC is medium pressure liquid chromatography; DMSO is dimethylsulfoxide; $CDCl_3$ is deuterated chloroform; MS is mass spectroscopy; ESP is electrospray; EI is electron impact; CI is chemical ionisation; EtOAc is ethyl acetate; MeOH is methanol.

Each of the following Examples comprises an independent aspect of the invention.

EXAMPLE 1

(5RS)-3-(3-Fluoro-4-thiomorpholin-4-ylphenyl)-5-(1,2,3-triazol-1-ylmethyl)-4,5-dihydroisoxazole A mixture of (5RS)-3-(3,4-difluorophenyl)-5-(1,2,3-triazol-1-ylmethyl)-4,5-dihydroisoxazole (528 mg, 2 mM), potassium carbonate (414 mg, 3 mM), and thiomorpholine (7.5 ml) was heated under nitrogen at 130° for 40 hours. After cooling, the mixture was partitioned between water (150 ml) and ethyl acetate (150 ml). The organic extract was washed with aqueous sodium dihydrogen phosphate (75 ml), sodium bicarbonate (75 ml), and brine (75 ml). After drying (magnesium sulfate) and evaporation, the crude product was then purified by chromatography on a 20 g silica Mega Bond Elut® column, eluting with a gradient from 50–100% ethyl acetate in isohexane. Relevant fractions were combined to give the desired product (305 mg).

MS (ESP): 348 ($MH^+$) for $C_{16}H_{18}FN_5OS$ NMR (DMSO-$d_6$) δ: 2.72 (t, 4H); 3.21 (dd, 1H); 3.31 (t overlapping $H_2O$, 4H); 3.53 (dd, 1H); 4.61 (m, 2H); 5.10 (m, 1H); 7.08 (t, 1H); 7.32 (overlapping m, 2H); 7.71 (d, 1H); 8.11 (d, 1H).

The intermediate for this compound was prepared as follows:—

(5RS)-3-(3,4-Difluorophenyl)-5-(1,2,3-triazol-1-ylmethyl)-4,5-dihydroisoxazole

A solution of 1-allyl-1,2,3-triazole (456 mg, 4.18 mM; see Annalen, 1965, 688, 205) and 3,4-difluorobenzohydroximinoyl chloride (800 mg, 4.18 mM) in anhydrous diethyl ether (50 ml) under a nitrogen atmosphere was treated dropwise with a solution of dry triethylamine (549 mg, 5.43 mM) in anhydrous diethyl ether (10 ml) over 20 minutes. A copious white precipitate formed, and the mixture was stirred for 18 hours. The mixture was treated with ethyl acetate (80 ml) and brine (50 ml), the organic layer separated, and washed with brine (100 ml). After drying (magnesium sulfate) and evaporation, the crude product was purified by chromatography on a 50 g silica Mega Bond Elut® column, eluting with a gradient from 0–5% methanol in dichloromethane. Relevant fractions were combined to give the desired product (837 mg).

MS (ESP): 265 (MH$^+$) for $C_{12}H_{10}F_2N_4O$ NMR (DMSO-$d_6$) δ: 3.27 (dd, 1H); 3.58 (dd, 1H); 4.63 (d, 2H); 5.16 (m, 1H); 7.47 (dd, 1H); 7.52 (t, 1H); 7.68 (dd, 1H); 7.71 (d, 1H); 8.11 (d, 1H).

EXAMPLE 2

(5RS)-3-(3-Fluoro-4-(1-oxothiomorpholin-4-yl)phenyl)-5-(1,2,3-triazol-1-ylmethyl)-4,5-dihydroisoxazole and (5RS)-3-(3-fluoro-4-(1,1-dioxothiomorpholin-4-yl)phenyl)-5-(1,2,3-triazol-1-ylmethyl)-4,5-dihydroisoxazole To a stirred solution of (5RS)-3-(3-fluoro-4-thiomorpholin-4-yl phenyl)-5-(1,2,3-triazol-1-ylmethyl)-4,5-dihydroisoxazole (200 mg, 0.58 mM) in dichloromethane (7.5 ml) was added dropwise a solution of 3-chloroperoxybenzoic acid (90%, 151 mg, 0.79 mM) in dichloromethane (7.5 ml) at ambient temperature, and stirring continued for 1 hour. Aqueous sodium metabisulfite (5%, 7.5 ml) was added, and after stirring for 5 minutes the organic phase was separated. After further extraction with dichloromethane (2×15 ml), the combined extracts were washed with aqueous sodium bicarbonate solution (2×15 ml) and dried (magnesium sulfate). Crude product was chromatographed on a 20 g silica Mega Bond Elut® column, eluting first with 1% methanol in dichloromethane to give the sulfone (5RS)-3 -(3-fluoro-4-(1,1-dioxothiomorpholin-4-yl)phenyl)-5-(1,2,3-triazol-1-ylmethyl)-4,5-dihydroisoxazole (42 mg).

MS (ESP): 380 (MH$^+$) for $C_{16}H_{18}FN_5O_3S$ NMR (DMSO-$d_6$) δ: 3.22 (overlapping dd+m+H$_2$O, ~5H); 3.53 (dd, 1H); 3.56 (m, 4H); 4.61 (m, 2H); 5.13 (m, 1H); 7.18 (t, 1H); 7.36 (overlapping m, 2H); 7.71 (d, 1H); 8.11 (d, 1H).

Further elution with 5% methanol in dichloromethane gave the more polar sulfoxide (5RS)-3-(3-fluoro-4-(1-oxothiomorpholin-4-yl)phenyl)-5-(1,2,3-triazol-1-ylmethyl)-4,5-dihydroisoxazole (158 mg).

MS (ESP): 364 (MH$^+$) for $C_{16}H_{18}FN_5O_2S$ NMR (DMSO-$d_6$) δ: 2.82 (dm, 2H); 3.01 (tm, 2H); 3.22 (dd, 1H); 3.33 (dm, 2H); 3.53 (dd, 1H); 3.61 (t, 2H); 4.60 (m, 2H); 5.11 (m, 1H); 7.18 (t, 1H); 7.36 (overlapping m, 2H); 7.71 (d, 1H); 8.11 (d, 1H).

EXAMPLE 3

(5RS)-3-(3-Fluoro-4-morpholin-4-ylphenyl)-5-(1,2,3-triazol-1-ylmethyl)-4,5-dihydroisoxazole (5RS)-3-(3,4-Difluorophenyl)-5-(1,2,3-triazol-1-ylmethyl)-4,5-dihydroisoxazole (264 mg, 1 mM) was treated with morpholine essentially as in Example 1. Work-up of the dried organic solution gave the desired product (325 mg) of sufficient purity.

MS (ESP): 332 (MH$^+$) for $C_{16}H_{18}FN_5O_2$ NMR (DMSO-$d_6$) δ: 3.04 (t, 4H); 3.22 (dd, 1H); 3.53 (dd, 1H); 3.72 (t, 4H); 4.58 (dd, 1H); 4.64 (dd, 1H); 5.10 (m, 1H); 7.03 (t, 1H); 7.32 (overlapping m, 2H); 7.70 (d, 1H); 8.11 (d, 1H).

EXAMPLE 4

(5RS)-3-(3-Fluoro-4-imidazol-1-ylphenyl)-5-(1,23-triazol-1-yl-methyl)-4,5-dihydroisoxazole A slurry of sodium hydride (60% in oil, 44 mg, 1.1 mM) in anhydrous N,N-dimethylformamide (1 ml) was stirred under an atmosphere of nitrogen and treated dropwise with a solution of imidazole (76 mg, 1.1 mM) in anhydrous N,N-dimethylformamide (1 ml) at 0°. The mixture was allowed to warm to ambient temperature over 20 minutes, then a solution of (5RS)-3-(3,4-difluorophenyl)-5-(1,2,3-triazol-1-yl-methyl)- 4,5-dihydroisoxazole (264 mg, 1 mM) in anhydrous N,N-dimethylformamide (2 ml) added, and the mixture stirred at 70° for 16 hours. After cooling, the mixture was partitioned between aqueous sodium bicarbonate solution (40 ml) and ethyl acetate (40 ml), and the organic extract washed with water (40 ml) and brine (40 ml). After drying (magnesium sulfate) and evaporation, the crude product was chromatographed on a 20 g silica Mega Bond Elut® column, eluting with 2.5% methanol in dichloromethane. Relevant fractions were combined to give the desired product (90 mg).

MS (ESP): 313 (MH$^+$) for $C_{15}H_{13}FN_6O$ NMR (DMSO-$d_6$) δ: 3.31 (dd overlapping H$_2$O, 1H); 3.63 (dd, 1H); 4.66 (d, 2H); 5.20 (m, 1H); 7.13 (d, 1H); 7.58 (dd, 1H); 7.60 (dd, 1H); 7.72 (overlapping m, 3H); 8.08 (d, 1H); 8.13 (d, 1H).

EXAMPLE 5

(5RS)-3-(3-Fluoro-4-pyrazol-1-ylphenyl)-5-(1,2,3-triazol-1-yl-methyl)-4,5-dihydroisoxazole A slurry of sodium hydride (60% in oil, 44 mg, 1.1 mM) in anhydrous N,N-dimethylformamide (1 ml) was stirred under an atmosphere of nitrogen and treated dropwise with a solution of pyrazole (76 mg, 1.1 mM) in anhydrous N,N-dimethylformamide (1 ml) at 0°. The mixture was allowed to warm to ambient temperature over 20 minutes, then a solution of (5RS)-3-(3,4-difluorophenyl)-5-(1,2,3-triazol-1-yl-methyl)-4,5-dihydroisoxazole (264 mg, 1 mM) in anhydrous N,N-dimethylformamide (2 ml) added, and the mixture stirred at 70° for 16 hours. After cooling, the mixture was partitioned between aqueous sodium bicarbonate solution (40 ml) and ethyl acetate (40 ml), and the organic extract washed with water (40 ml) and brine (40 ml). After drying (magnesium sulfate) and evaporation, the crude product was chromatographed on a 20 g silica Mega Bond Elut® column, eluting with ethyl acetate. Relevant fractions were combined to give the desired product (141 mg).

MS (ESP): 313 (MH$^+$) for $C_{15}H_{13}FN_6O$ NMR (DMSO-$d_6$) δ: 3.32 (dd overlapping H$_2$O, 1H); 3.62 (dd, 1H); 4.65 (d, 2H); 5.19 (m, 1H); 6.59 (t, 1H); 7.60 (dd, 1H); 7.68 (dd, 1H); 7.72 (d, 1H); 7.83 (d, 1H); 7.90 (t, 1H); 8.13 (d, 1H); 8.25 (t, 1H).

EXAMPLE 6

(5RS)-3-(3-Fluoro-4-(1,2,3-triazol-1-yl)phenyl)-5-(1,2,3-triazol-1-yl-methyl)-4,5-dihydroisoxazole A slurry of sodium hydride (60% in oil, 44 mg, 1.1 mM) in anhydrous N,N-dimethylformamide (1 ml) was stirred under an atmosphere of nitrogen and treated dropwise with a solution of 1,2,3-triazole (76 mg, 1.1 mM) in anhydrous N,N-dimethylformamide (1 ml) at 0°. The mixture was allowed to warm to ambient temperature over 20 minutes, then a solution of (5RS)-3-(3,4-difluorophenyl)-5-(1,2,3-triazol-1-yl-methyl)-4,5-dihydroisoxazole (264 mg, 1 mM) in anhydrous N,N-dimethylformamide (2 ml) added, and the mixture stirred at 70° for 16 hours. After cooling, the mixture was partitioned between aqueous sodium bicarbonate solution (40 ml) and ethyl acetate (40 ml), and the organic extract washed with water (40 ml) and brine (40 ml). After drying (magnesium sulfate) and evaporation, the crude product was chromatographed on a 20 g silica Mega Bond Elut® column, eluting with ethyl acetate. Relevant fractions were combined to give the desired product (12 mg).

MS (ESP): 314 (MH$^+$) for $C_{14}H_{12}FN_7O$ NMR (DMSO-$d_6$) δ: 3.34 (dd, 1H); 3.65 (dd, 1H); 4.66 (d, 2H); 5.22 (m, 1H); 7.67 (dd, 1H); 7.72 (d, 1H); 7.77 (dd, 1H); 7.93 (t, 1H); 8.01 (d, 1H); 8.13 (d, 1H); 8.63 (d, 1H).

EXAMPLE 7

(5RS)-3-(3-Fluoro-4-piperazin-1-ylphenyl)-5-(1,2,3-triazol-1-yl-methyl)-4,5-dihydroisoxazole A mixture of (5RS)-3-(3,4-difluorophenyl)-5-(1,2,3-triazol-1-ylmethyl)-4,5-dihydroisoxazole (528 mg, 2 mM), potassium carbonate (414 mg, 3 mM), and piperazine (7.5 g) was heated under nitrogen at 130° for 4 hours. After cooling, the mixture was partitioned between water (150 ml) and ethyl acetate (150 ml). The organic extract was washed with sodium bicarbonate (75 ml), and brine (75 ml). After drying (magnesium sulfate) and evaporation, the desired product (614 mg) was obtained sufficiently pure without chromatography. MS (ESP): 331 (MH$^+$) for $C_{16}H_{19}FN_6O$ NMR (DMSO-$d_6$) δ: 2.81 (t, 4H); 2.97 (t, 4H); 3.20 (dd overlapped by H$_2$O, 1H); 3.52 (dd, 1H); 4.58 (dd, 1H); 4.64 (dd, 1H); 5.08 (m, 1H); 7.02 (t, 1H); 7.30 (overlapping m, 2H); 7.70 (d, 1H); 8.11 (d, 1H); NH missing—exchanged.

EXAMPLE 8

(5RS)-3-(3-Fluoro-4-(4-methanesulfonyl)piperazin-1-ylphenyl)-5-(1,2,3-triazol-1-ylmethyl)-4,5-dihydroisoxazole (5RS)-3-(3-Fluoro-4-piperazin-1-ylphenyl)-5-(1,2,3-triazol-1-ylmethyl)-4,5-dihydroisoxazole (100 mg, 0.303 mM) in dichloromethane (2.5 ml) at 0° was treated with aqueous sodium bicarbonate (5%, 2.5 ml), and the mixture stirred vigorously. An excess of methanesulfonyl chloride (300 mg, 2.6 mM) was added, and the mixture was allowed to come to ambient temperature while stirring for 16 hours. The mixture was diluted with dichloromethane (15 ml) and water (15 ml), the organic layer separated, and washed successively with water (15 ml) and brine (15 ml). After drying (magnesium sulfate) and evaporation, the crude product was chromatographed on a 10 g silica Mega Bond Elut® column, eluting with 2.5% methanol in dichloromethane. Relevant fractions were combined to give the desired product (69 mg). MS (ESP): 409 (MH$^+$) for $C_{17}H_{21}FN_6O_3S$ NMR (DMSO-$d_6$) δ: 2.92 (s, 3H); 3.16 (t, 4H); 3.25 (m overlapped by H$_2$O, 5H); 3.54 (dd, 1H); 4.58 (dd, 1H); 4.64 (dd, 1H); 5.11 (m, 1H); 7.09 (t, 1H); 7.35 (dd, 1H); 7.39 (dd, 1H); 7.70 (d, 1H); 8.11 (d, 1H).

EXAMPLE 9

(5RS)-3-(3-Fluoro-4-(4-acetyl)piperazin-1-ylphenyl)-5-(1,2,3-triazol-1-ylmethyl)-4,5-dihydroisoxazole (5RS)-3-(3-Fluoro-4-piperazin-1-ylphenyl)-5-(1,2,3-triazol-1-ylmethyl)-4,5-dihydroisoxazole (100 mg, 0.303 mM) was treated with acetic anhydride essentially as in Example 8, to give the desired product (93 mg) after chromatography.

MS (ESP): 373 (MH$^+$) for $C_{18}H_{21}FN_6O_2$ NMR (DMSO-$d_6$) δ: 2.02 (s, 3H); 3.01 (t, 2H); 3.07 (t, 2H); 3.22 (dd overlapped by H$_2$O, 1H); 3.53 (dd, 1H); 3.57 (m, 4H); 4.58 (dd, 1H); 4.64 (dd, 1H); 5.10 (m, 1H); 7.06 (t, 1H); 7.34 (dd, 1H); 7.37 (dd, 1H); 7.70 (d, 1H); 8.11 (d, 1H).

EXAMPLE 10

(5RS)-3-(3-Fluoro-4-(4-methoxycarbonyl)piperazin-1-ylphenyl)-5-(1,2,3-triazol-1-ylmethyl)-4,5-dihydroisoxazole (5RS)-3-(3-Fluoro-4-piperazin-1-ylphenyl)-5-(1,2,3-triazol-1-ylmethyl)-4,5-dihydroisoxazole (100 mg, 0.303 mM) was treated with methyl chloroformate essentially as in Example 8, to give the desired product (109 mg) after chromatography.

MS (ESP): 389 (MH$^+$) for $C_{18}H_{21}FN_6O_3$ NMR (DMSO-$d_6$) δ: 3.03 (t, 4H); 3.22 (dd overlapped by H$_2$O, 1H); 3.51 (overlapping m, 5H); 3.61 (s, 3H); 4.60 (m, 2H); 5.11 (m, 1H); 7.06 (t, 1H); 7.33 (dd, 1H); 7.37 (dd, 1H); 7.70 (d, 1H); 8.10 (d, 1H).

The invention claimed is:

1. A compound of the formula (I), or a pharmaceutically-acceptable salt, or an in-vivo-hydrolysable ester thereof,

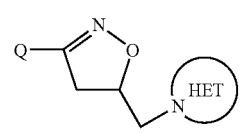

(I)

wherein
HET is an N-linked 5-membered, fully or partially unsaturated heterocyclic ring consisting of 3 nitrogen atoms, which ring is optionally substituted on a C atom, other than a C atom adjacent to the linking N atom, by an oxo or thioxo group;
and/or which ring is optionally substituted on any available C atom, other than a C atom adjacent to the linking N atom, by a substituent Rs wherein;
Rs is
halogen, (1–4C)alkoxy, (2–4C)alkenyloxy, (2–4C)alkenyl, (2–4C)alkynyl, (3–6C)cycloalkyl, (3–6C)cycloalkenyl, amino, (1–4C)alkylamino, di-(1–4C)alkylamino, (2–4C)alkenylamino, (1–4C)alkylcarbonylamino, (1–4C)alkylthiocarbonylamino, (1–4C)alkyl-OCO—NH—, (1–4C)alkyl-NH—CO—NH—, (1–4C)alkyl-NH—CS—NH—, (1–4C)alkyl-SO$_2$—NH— or (1–4C)alkyl-S(O)q— (wherein q is 0, 1 or 2); fluoromethyl, difluoromethyl, trifluoromethyl, chloromethyl, bromomethyl, cyanomethyl, cyano, amino, azido or methylthiomethyl;
Q is:—

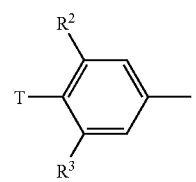

Q1 wherein R$^2$ and R$^3$ are independently hydrogen or fluoro;
wherein T is (TCc) an optionally substituted 6-membered monocyclic ring consisting of 2 heteroatoms independently selected from O, N and S (optionally oxidised), and linked via a ring nitrogen atom or a ring sp$^1$ or sp$^2$ carbon atom, which monocyclic ring is fully saturated other than (where appropriate) at a linking sp$^2$ carbon atom.

2. A compound of the formula (IB)

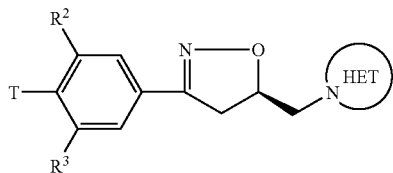
(IB)

wherein T, R2, R3, and HET are as defined in claim 1.

3. A compound of claim 2 wherein HET is 1,2,3-triazol-1-yl) or 1,2,4-triazol-1-yl.

4. A pharmaceutical composition which comprises a compound of claim 1, or a pharmaceutically-acceptable salt or an in-vivo hydrolysable ester thereof, and a pharmaceutically-acceptable diluent or carrier.

5. A process for the manufacture of a compound of claim 1 comprising one or more of the processes (a) to (h) below:
(a) by modifying a substituent in or introducing a substituent into another compound of formula (I).
(b) by reaction of a compound of formula (II):

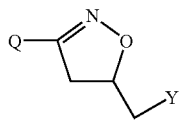
(II)

wherein Y is a displaceable group (which may be (i) generated in-situ, for example under Mitsunobu conditions, or (ii) preformed, such as chloro or mesylate) with a compound of the formula (III):

HET (III)

wherein HET is HET-H free-base form or HET-anion formed from the free base form; or
(c) by reaction of a compound of formula (IV):

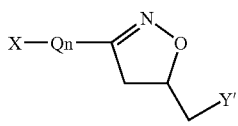
(IV)

wherein Y' is HET, X is a displaceable substituent and Qn is as defined herein for Q1–Q8 but with X in place of the substituent T; with a compound of the formula (V):

T (V)

wherein T is T-H free-base form or T-anion formed from the free base form T-H as hereinabove defined for T; or
(d) by reaction of a compound of the formula (VI):

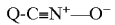
Q-C≡N$^+$—O$^-$ (VI)

wherein the group C≡N$^+$—O$^-$ is a nitrile oxide; with an allylic derivative such as an olefin of the formula (VII):

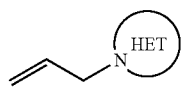
(VII)

(e) by transition metal mediated coupling of a compound of formula (IV), wherein Y' is HET, X is a replaceable substituent (such as trimethylstannyl) and Qn is as defined herein for Q1–Q8 but with X in place of the substituent T; with a compound of the formula (VIII):

T-X' (VIII)

wherein X and X' are complementary substitutents capable of entering into such coupling reactions; or
(f) for HET as optionally substituted 1,2,3-triazole by cycloaddition via the azide (wherein e.g. Y in (II) is azide) to acetylenes, or to acetylene equivalents such as optionally substituted cylcohexa-1,4-dienes or optionally substituted ethylenes bearing eliminatable substituents such as arylsulfonyl; or
(g) for HET as 4-substituted 1,2,3-triazole compounds of formula (I) may be made by reacting aminomethylisoxazolines with 1,1-dihaloketone sulfonylhydrazones;
(h) for HET as 4-substituted 1,2,3-triazole compounds of formula (I) may also be made by reacting azidomethyl isoxazolines with terminal alkynes using Cu(1) catalysis; and thereafter if necessary: (i) removing any protecting groups; (ii) forming a pharmaceutically-acceptable salt; (iii) forming an in-vivo hydrolysable ester.

6. A compound selected from
(5RS)-3-(3-Fluoro-4-thiomorpholin-4-yl phenyl)-5-(1,2,3-triazol-1-ylmethyl)-4,5-dihydroisoxazole;
(5RS)-3-(3-Fluoro-4-(1-oxothiomorpholin-4-yl)phenyl)-5-(1,2,3-triazol-1-ylmethyl)-4,5-dihydroisoxazole;
(5RS)-3-(3-fluoro-4-(1,1-dioxothiomorpholin-4-yl)phenyl)-5-(1,2,3-triazol-1-ylmethyl)-4,5-dihydroisoxazole;
(5RS)-3-(3-Fluoro-4-morpholin-4-yl phenyl)-5-(1,2,3-triazol-1-ylmethyl)-4,5-dihydroisoxazole;
(5RS)-3-(3-Fluoro-4-piperazin-1-ylphenyl)-5-(1,2,3-triazol-1-ylmethyl)-4,5-dihydroisoxazole;
(5RS)-3-(3-Fluoro-4-(4-methanesulfonyl)piperazin-1-ylphenyl)-5-(1,2,3-triazol-1-ylmethyl)-4,5-dihydroisoxazole;
(5RS)-3-(3-Fluoro-4-(4-acetyl)piperazin-1-ylphenyl)-5-(1,2,3-triazol-1-ylmethyl)-4,5-dihydroisoxazole; and
(5RS)-3-(3-Fluoro-4-(4-methoxycarbonyl)piperazin-1-ylphenyl)-5-(1,2,3-triazol-1-ylmethyl)-4,5-dihydroisoxazole;

or a pharmaceutically acceptable salt or an in-vivo hydrolysable ester thereof.

* * * * *